(12) United States Patent
Oroskar et al.

(10) Patent No.: US 12,173,254 B2
(45) Date of Patent: Dec. 24, 2024

(54) PROCESS FOR PURIFYING LPC-DHA AND/OR LPC-EPA USING A CHROMATOGRAPHIC STATIONARY PHASE AND COMPOSITIONS THEREOF

(71) Applicant: Orochem Technologies Inc., Naperville, IL (US)

(72) Inventors: Anil Rajaram Oroskar, Oak Brook, IL (US); Babu Siddegowda Antharavally, Caledonia, IL (US); Asha Anil Oroskar, Oak Brook, IL (US)

(73) Assignee: Orochem Technologies Inc., Naperville, IL (US)

( * ) Notice: Subject to any disclaimer, the term of this patent is extended or adjusted under 35 U.S.C. 154(b) by 191 days.

(21) Appl. No.: 17/545,747

(22) Filed: Dec. 8, 2021

(65) Prior Publication Data
US 2022/0177806 A1    Jun. 9, 2022

Related U.S. Application Data

(60) Provisional application No. 63/122,871, filed on Dec. 8, 2020.

(51) Int. Cl.
*C11B 3/10* (2006.01)
*A61K 31/685* (2006.01)
*B01D 15/26* (2006.01)

(52) U.S. Cl.
CPC .............. *C11B 3/10* (2013.01); *A61K 31/685* (2013.01); *B01D 15/265* (2013.01);
(Continued)

(58) Field of Classification Search
CPC ....... C11B 3/10; A61K 31/685; B01D 15/265; B01D 2253/304; B01D 2253/306;
(Continued)

(56) References Cited

U.S. PATENT DOCUMENTS

| | | | |
|---|---|---|---|
| 2,985,589 A | 5/1961 | Broughton et al. | |
| 2018/0325924 A1* | 11/2018 | Subbaiah | A61K 9/1075 |
| 2019/0201424 A1* | 7/2019 | Hoem | A61K 31/685 |

FOREIGN PATENT DOCUMENTS

| | | |
|---|---|---|
| WO | WO 2020/254675 A1 | 12/2020 |
| WO | WO 2021/202680 A2 | 10/2021 |
| WO | WO 2021/202680 A3 | 10/2021 |

OTHER PUBLICATIONS

Sugasini Dhavamani et al: "Efficient Enrichment of Retinal DHA with Dietary Lysophosphatidylcholine-DHA: Potential Application for Retinopathies", NUTRIENTS, vol. 12, No. 10, 2020, p. 3114.*

(Continued)

*Primary Examiner* — Deborah D Carr
(74) *Attorney, Agent, or Firm* — Leydig, Voit & Mayer, Ltd.

(57) ABSTRACT

Embodiments of a method of purifying a lysophosphatidylcholine (e.g., LPC-DHA and/or LPC-EPA) from a composition containing the lysophosphatidylcholine and at least one impurity, e.g., from phospholipids, free fatty acids, triacylglycerols (TAGs), diacylglycerols (DAGs), monoacylglycerols (MAGs), glycerol, sterols, tocopherols, vitamin A, flavonoids, and minerals can use a continuous simulated moving bed process, a batch column chromatography method, or a single column to provide a purified composition of the lysophosphatidylcholine. The purified lysophosphatidylcholine (e.g., LPC-DHA and/or LPC-EPA) products can be used in various pharmaceutical and nutraceutical applications, e.g., for treating and/or preventing a neurological disease or disorder.

15 Claims, 12 Drawing Sheets

(52) U.S. Cl.
CPC .. *B01D 2253/304* (2013.01); *B01D 2253/306* (2013.01); *B01D 2253/308* (2013.01); *B01D 2253/311* (2013.01)

(58) Field of Classification Search
CPC ........ B01D 2253/308; B01D 2253/311; B01D 15/1821; B01D 15/327; B01J 2220/603; B01J 20/28004; B01J 20/28011; B01J 20/28057; B01J 20/28078; A23V 2250/1846; A23V 2250/1868; A23V 2250/187; A23V 2250/2042; A23J 7/00; A23L 33/115; A23D 9/013
See application file for complete search history.

(56) References Cited

OTHER PUBLICATIONS

Di Marzo et al., "Dietary krill oil increases docosahexaenoic acid and reduces 2-arachidonoylglycerol but not N-acylethanolamine levels in the brain of obese Zucker rats," *International Dairy Journal*, 20(4): 231-235 (2010).

Graf et al., "Age dependent incorporation of $^{14}$C-DHA into rat brain and body tissues after dosing various $^{14}$C-DHA-esters," *Prostaglandins, Leukotrienes and Essential Fatty Acids*, 83(2): 89-96, Abstract (2010).

Le Grandois et al., "Investigation of Natural Phosphatidylcholine Sources: Separation and Identification by Liquid Chromatography-Electrospray Ionization-Tandem Mass Spectrometry (LC-ESI-MS$^2$) of Molecular Species," *J. Agric. Food Chem.*, 57: 6014-6020 (2009).

Nguyen et al., "Mfsd2a is a transporter for the essential omega-3 fatty acid docosahexaenoic acid" *Nature*, 509: 503-506 (2014).

Ramprasath et al., "Supplementation of krill oil with high phospholipid content increases sum of EPA and DHA in erythrocytes compared with low phospholipid krill oil, " *Lipids in Health and Disease*, 14: 142 (2015).

Rossmeisl et al., "Metabolic Effects of n-3 PUFA as Phospholipids Are Superior to Triglycerides in Mice Fed a High-Fat Diet: Possible Role of Endocannabinoids," *PloS One*, 7(6): e38834 (2012).

Saini et al., "Omega-3 and omega-6 polyunsaturated fatty acids: Dietary sources, metabolism, and significance—A Review," *Life Sciences*, 203: 253-267 (2018).

Sugasini et al., "Dietary docosahexaenoic acid (DHA) as lysophosphatidylcholine, but not as free acid, enriches brain DHA and improves memory in adult mice," *Nature, Scientific Reports*, 7(1): 11263 (2017).

Sugasini et al., "Efficient Enrichment of Retinal DHA with Dietary Lysophosphatidylcholine-DHA: Potential Application for Retinopathies," *Nutrients*, 12(10): 3114 (2020).

Winther et al. "Elucidation of Phosphatidylcholine Composition in Krill Oil Extracted from *Euphausia superba*," Lipids, 46: 25-36 (2010).

Yalagala et al., "Lipase Treatment of Dietary Krill Oil, but Not Fish Oil, Enables Enrichment of Brain Eicosapentaenoic Acid and Docosahexaenoic Acid," *Mol. Nutr. Food Res.*, 64(12): e2000059 (2020).

European Patent Office, International Search Report and Written Opinion of the International Searching Authority in International Patent Application No. PCT/US2021/062438 (Mar. 10, 2022).

\* cited by examiner

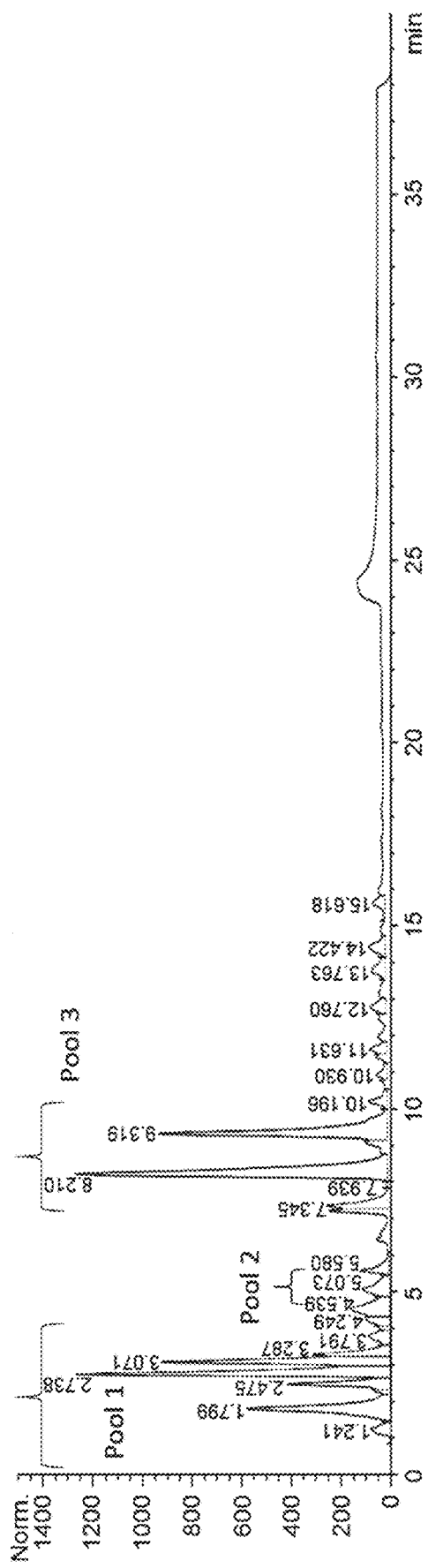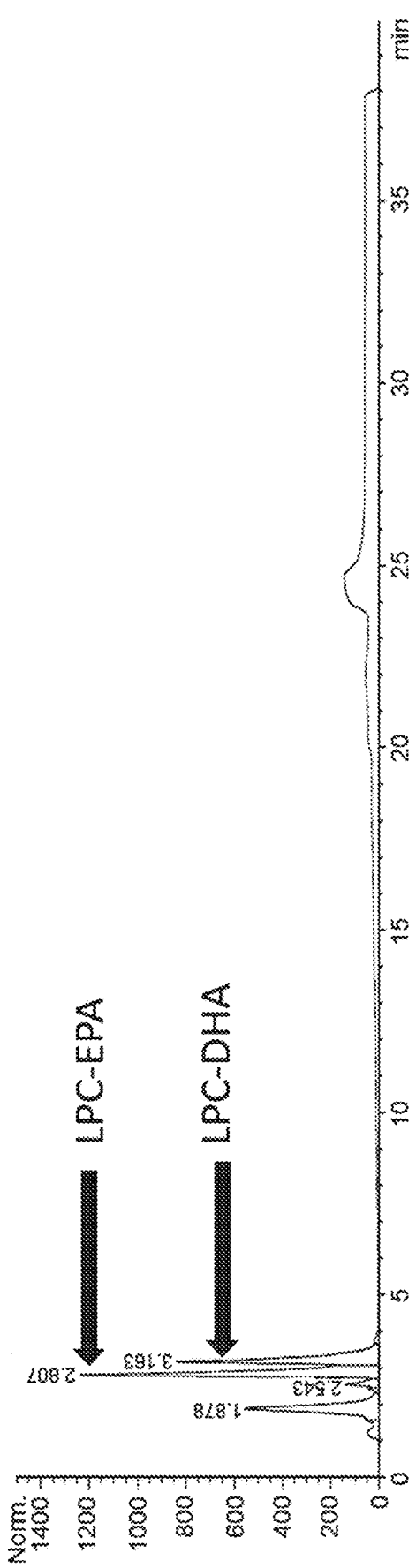
FIG. 4A
FIG. 4B

PROCESS FOR PURIFYING LPC-DHA AND/OR LPC-EPA USING A CHROMATOGRAPHIC STATIONARY PHASE AND COMPOSITIONS THEREOF

CROSS-REFERENCE TO RELATED APPLICATIONS

This patent application claims the benefit of U.S. Provisional Application No. 63/122,871, filed Dec. 8, 2020, and entitled, "Process for Purifying LPC-DHA and/or LPC-EPA using a Chromatographic Stationary Phase and Compositions Thereof," which is incorporated in its entirety herein by this reference.

BACKGROUND

The present disclosure relates to processes for purifying a lysophosphatidylcholine and, more particularly, to methods of purifying a lysophosphatidylcholine (e.g., lysophosphatidylcholine-docosahexaenoic acid (LPC-DHA) and/or lyso-phophatidylcholine-eicosapentaenoic acid (LPC-EPA)) from a composition containing the lysophosphatidylcholine and at least one impurity.

Marine n-3 polyunsaturated fatty acids (PUFAs) including eicosapentaenoic acid (EPA) and docosahexaenoic acid (DHA) have been demonstrated to play beneficial roles in prevention of several diseases. Conventionally, consumption of n-3 PUFAs like EPA and DHA occurs mainly through fish oil or krill oil supplements as these are rich in omega-3 fatty acids, predominantly EPA and DHA. Typically, n-3 PUFAs obtained from fish oil are esterified to glycerol of triglycerides (TGs), whereas in krill oil, n-3 PUFAs are esterified to glycerol of phospholipids (PLs). Krill oil can contain particularly rich amounts of choline-containing phospholipids with a phosphatidylcholine (PC) concentration of about 34 grams per 100 grams of oil (Grandois et al, *J. Agric. Food Chem.*, 2009, 57, 6014-6020 and Winther et al, *Lipids*, 2010, 46, 25-36). For example, Krill oil extract prepared from a species of Antarctic krill, *Euphasia superba*, can contain approximately 60-70% of the omega-3 fatty acids, which are bound to PLs (Ramprasanth et al., *Lipids in Health and Disease*, 2015, 14:142).

Fish oil has been recommended and used to improve Alzheimer's disease (AD) and related dementia (ADRD) and other neurological disorders, likely motivated by components, DHA and EPA. While current dietary supplements (e.g., fish oil and krill oil) increase n-3 fatty acids such as DHA in certain body tissues, they do not appreciably increase DHA in the brain, as they are hydrolyzed to free DHA and are absorbed as triacylglycerol. Several studies have shown efficient uptake of n-3 fatty acids into target organs such as heart, brain and liver when attached to PLs as in krill oil compared to TGs as in fish oil (Rossmeisl et al., *PloS one*, 2012, 7(6), e38834; Graf et al., *Prostaglandins, Leukotrienes and Essential Fatty Acids*, 2010, 83(2) 89-96; Di Marzo et al., *International Dairy Journal*, 2010, 20(4), 231-235; Nguyen et al., *Nature*, 2014, 509, 503-506; Sugasini et al., *Nature, Scientific Reports*, 2017, 7(1), 11263; Subbaiah et al., U.S. Patent Application Publication 2018/0325924). The recent demonstration of a transporter at the blood brain barrier (Mfsd2a), which specifically transports lysophosphatidylcholine-DHA (LPC-DHA), but not free DHA, further supports the mechanism that the brain uniquely takes up DHA in the form of LPC-DHA (Nguyen et al., *Nature*, 2014, 509, 503-506). In addition, recent studies in mice have demonstrated that the DHA content of most regions of the brain was increased significantly by feeding either sn-1 or sn-2 LPC-DHA, but not by feeding free DHA, which however, has been shown to enrich DHA content in other tissues (Sugasini et al., *Nature, Scientific Reports*, 2017, 7(1), 11263; and Subbaiah et al., U.S. Patent Application Publication 2018/0325924).

Thus there is a need for compositions (e.g., pharmaceuticals and nutraceuticals), which can be produced on an industrial scale, capable of increasing delivery of n-3 PUFAs like EPA and DHA to the brain. It will be appreciated that this background description has been created by the inventors to aid the reader and is not to be taken as an indication that any of the indicated problems were themselves appreciated in the art. While the described principles can, in some aspects and embodiments, alleviate the problems inherent in other systems, it will be appreciated that the scope of the protected innovation is defined by the attached claims and not by the ability of any disclosed feature to solve any specific problem noted herein.

SUMMARY

In one aspect, the present disclosure is directed to the preparation and purification of compositions containing lysophosphatidylcholines such as sn-1 or sn-2 LPC-DHA and/or sn-1 or sn-2 LPC-EPA. In some aspects, the present disclosure is directed to embodiments of a method for purifying a lysophosphatidylcholine from a composition containing the lysophosphatidylcholine and at least one impurity. For example, in embodiments, methods following principles of the present disclosure can be used to separate a desired lysophosphatidylcholine (e.g., lysophosphatidylcholine-docosahexaenoic acid (LPC-DHA) and/or lysophophatidylcholine-eicosapentaenoic acid (LPC-EPA)), i.e., to increase its purity, from other compounds such as phospholipids, free fatty acids, triacylglycerols (TAGs), diacylglycerols (DAGs), monoacylglycerols (MAGs), glycerol, sterols, tocopherols, vitamin A, flavonoids, minerals, and mixtures thereof.

In some aspects, the present disclosure is directed to embodiments of a method for purifying a lysophosphatidylcholine obtained from an enzymatic conversion of a phosphatidylcholine (e.g., a phosphatidylcholine containing docosahexaenoic acid and/or a phosphatidylcholine containing eicosapentaenoic acid). In some embodiments, the phosphatidylcholine is obtained from natural sources such as krill oil. In certain embodiments, the phosphatidylcholine is obtained synthetically. In other aspects, the present disclosure is directed to embodiments of a method for purifying a lysophosphatidylcholine obtained synthetically.

In some aspects, the present disclosure is directed to embodiments of a method for purifying a lysophosphatidylcholine (e.g., lysophosphatidylcholine-docosahexaenoic acid (LPC-DHA) and/or lysophophatidylcholine-eicosapentaenoic acid (LPC-EPA)) from a composition containing the lysophosphatidylcholine and at least one impurity. In one embodiment, the method includes preparing a feedstock stream that includes the composition. The feedstock stream is passed through one or more stationary phases to provide an eluate stream having a higher purity of the lysophosphatidylcholine than in the feedstock stream. In some embodiments, the stationary phase is a hydrophobic adsorbent (e.g., a polystyrene-divinylbenzene adsorbent, a polydivinylbenzene adsorbent, or a combination thereof) having one or more of the following properties: an average particle diameter of 20 microns to 600 microns, an average surface area of 300 m²/g to 900 m²/g, an average porosity of 75 Å to 1000 Å, an average water content of 35% to 80%, an average bulk density of 0.45 g/mL to 0.9 g/mL, or any combination thereof.

In some aspects, the present disclosure is directed to a purified composition comprising at least 60 wt. % of the lysophosphatidylcholine (e.g., lysophosphatidylcholine-docosahexaenoic acid (LPC-DHA) and/or lysophophatidylcholine-eicosapentaenoic acid (LPC-EPA)), for example, at least 70 wt. % of the lysophosphatidylcholine, at least 80 wt. % of the lysophosphatidylcholine, at least 90 wt. % of the lysophosphatidylcholine, or at least 95 wt. % of the lysophosphatidylcholine.

In some aspects, the present disclosure is directed to a dietary supplement (e.g., a soft gel chewable) or a pharmaceutical composition comprising the purified composition of the lysophosphatidylcholine (e.g., lysophosphatidylcholine-docosahexaenoic acid (LPC-DHA) and/or lysophophatidylcholine-eicosapentaenoic acid (LPC-EPA)). The dietary supplement and/or pharmaceutical composition can be used for treating and/or preventing a neurological disease or disorder such as depression, dementia, a traumatic brain injury, Alzheimer's disease, or Parkinson's disease.

Further and alternative aspects and features of the disclosed principles will be appreciated from the following detailed description and the accompanying drawings. As will be appreciated, the systems and techniques for purifying a lysophosphatidylcholine from a composition containing the lysophosphatidylcholine and at least one impurity that are disclosed herein are capable of being carried out and used in other and different embodiments, and capable of being modified in various respects. Accordingly, it is to be understood that both the foregoing general description and the following detailed description are exemplary and explanatory only and do not restrict the scope of the appended claims.

BRIEF DESCRIPTION OF THE DRAWINGS

The accompanying drawings are included to provide a further understanding of the disclosure. The drawings illustrate embodiments of the disclosure and together with the description serve to explain principles of embodiments of the disclosure.

FIG. 4A is a high performance liquid chromatography (HPLC) chromatogram of krill oil after 24 hours of lipase digestion at 50° C. with collected Pools 1, 2, and 3 specified.

FIG. 4B is a high performance liquid chromatography (HPLC) chromatogram of purified LPC-EPA and LPC-DHA obtained from Pool 1 set forth in FIG. 4A.

Figure 1:
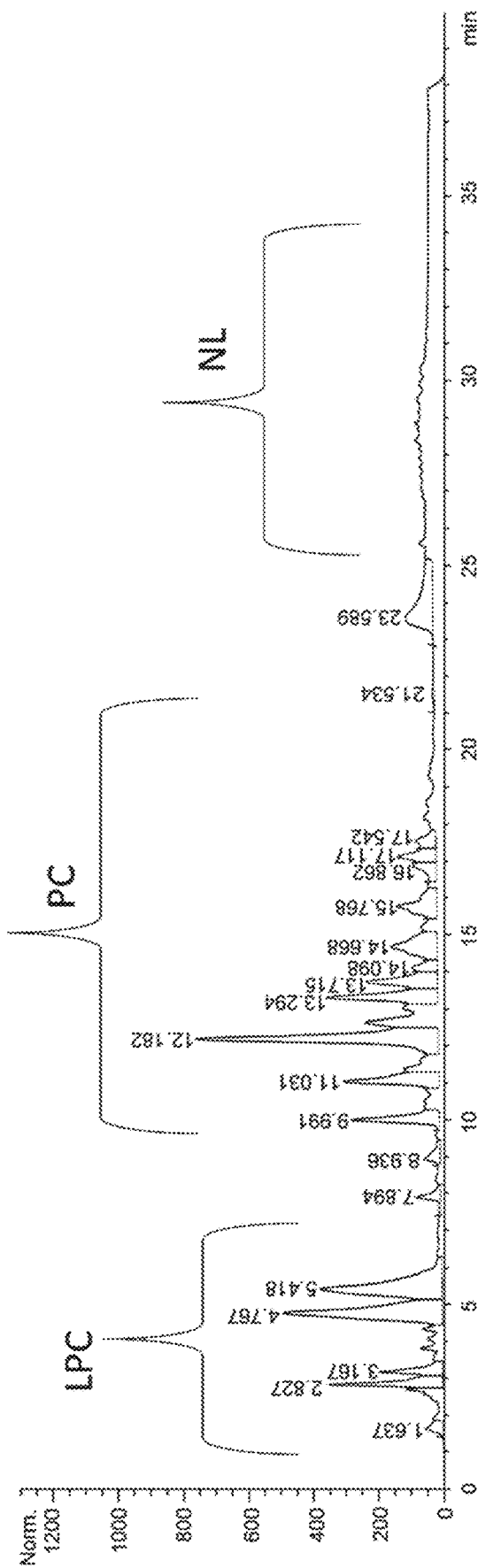
FIG. 1 is a high performance liquid chromatography (HPLC) chromatogram of krill oil before lipase digestion showing the mixture of lysophosphatidylcholines (LPCs), phosphatidylcholines (PCs), and neutral lipids (NLs).

DETAILED DESCRIPTION OF EXEMPLARY EMBODIMENTS n-3 polyunsaturated fatty acids (PUFAs) including eicosapentaenoic acid (EPA) and docosahexaenoic acid (DHA) have been demonstrated to play beneficial roles in prevention of several diseases. More particularly, n-3 PUFAs have been recommended as a dietary supplement to improve Alzheimer's disease (AD) and related dementia (ADRD), and other neurological disorders. DHA (docosahexaenoic acid) and EPA (eicosapentaenoic acid) are the two major omega 3 fatty acids (Om3FA) in the body, and have well recognized metabolically beneficial functions. Epidemiologic and experimental studies show that DHA, in particular, is beneficial for protection against age related cognitive decline and related dementia such as Alzheimer's disease, as the brain uniquely contains high concentration of DHA. While current dietary supplements (e.g., fish oil, krill oil, etc.) increase DHA in certain bodily tissues, they do not appreciably increase DHA in the brain.

Recent studies in mice have clearly demonstrated that the DHA content of most regions of the brain was increased significantly by feeding either sn-1 or sn-2 lysophosphatidylcholine-DHA, but not by feeding free DHA (Sugasini et al., *Nature, Scientific Reports*, 2017, 7(1), 11263).

In some aspects, the present disclosure provides methods to produce lysophosphatidylcholine (e.g., sn-1 or sn-2 LPC-DHA and/or sn-1 or sn-2 LPC-EPA) from naturally occurring precursors or synthetic compounds, as well as methods to purify the resulting lysophosphatidylcholine (e.g., sn-1 or sn-2 LPC-DHA and/or sn-1 or sn-2 LPC-EPA) from impurities such as phospholipids, free fatty acids, triacylglycerols (TAGs), diacylglycerols (DAGs), monoacylglycerols (MAGs), glycerol, sterols, tocopherols, vitamin A, flavonoids, minerals, and mixtures thereof. The purified lysophosphatidylcholine can be used in various pharmaceutical and nutraceutical applications. Other aspects of the present invention will be readily apparent from the disclosure provided herein.

In various embodiments, the present disclosure relates to a method of purifying a lysophosphatidylcholine from a composition containing the lysophosphatidylcholine and at least one impurity, the method comprising: passing a feedstock stream comprising the composition through at least one stationary phase to provide an eluate stream having a higher purity of the lysophosphatidylcholine than in the feedstock stream.

The composition containing lysophosphatidylcholine can be obtained from any suitable method and any suitable source (e.g., a synthetic source or natural source). In some embodiments, the lysophosphatidylcholine is obtained synthetically from one or more of phospholipids, choline, fatty acids, triacylglycerols (TAGs), diacylglycerols (DAGs), monoacylglycerols (MAGs), and glycerol. In other embodiments, the lysophosphatidylcholine is naturally produced or obtained from an enzymatic conversion of phosphatidylcholine to lysophosphatidylcholine. The phosphatidylcholine also can be obtained synthetically or naturally produced. For example, the phosphatidylcholine and/or the lysophosphatidylcholine can be obtained from natural sources such as fish oil, krill oil, egg, soybean, sunflower, and marine microalgae. In preferred embodiments, the natural source is krill oil.

As used herein, the term phosphatidylcholine (PC) refers to a compound of formula

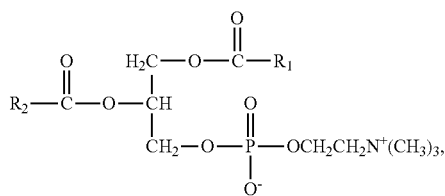

wherein $R_1$ and $R_2$ are hydrocarbon chains of fatty acids. In order to obtain lysophosphatidylcholine from phosphatidylcholine, fatty acid $R_1$ or fatty acid $R_2$ is removed, preferably by a lipase enzyme and/or a phospholipase enzyme. In preferred embodiments, the phosphatidylcholine comprises docosahexaenoic acid (DHA) or eicosapentaenoic acid (EPA) as fatty acid $R_1$ or fatty acid $R_2$. For example, phosphatidylcholine produced by krill oil has DHA and EPA enriched at the fatty acid $R_2$ position.

As used herein, the term lysophosphatidylcholine (LPC) refers to a compound of formula:

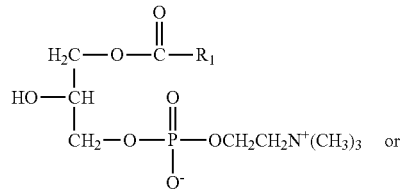

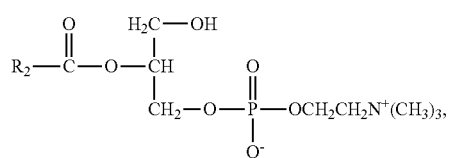

wherein $R_1$ and $R_2$ are hydrocarbon chains of fatty acids. In some embodiments, the lysophosphatidylcholine is lysophosphatidylcholine-docosahexaenoic acid (LPC-DHA), lysophophatidylcholine-eicosapentaenoic acid (LPC-EPA), or a combination thereof. Thus, the lysophosphatidylcholine can be one or more of the following compounds

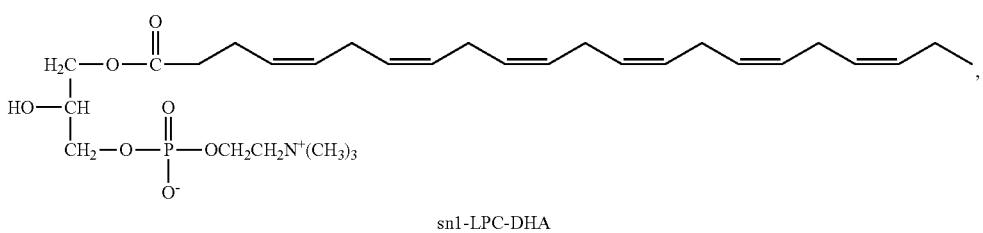

sn1-LPC-DHA

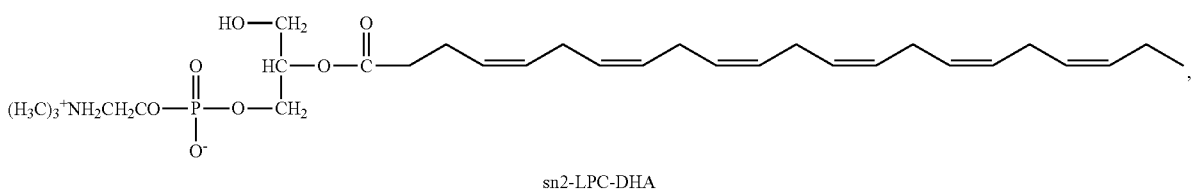

sn2-LPC-DHA

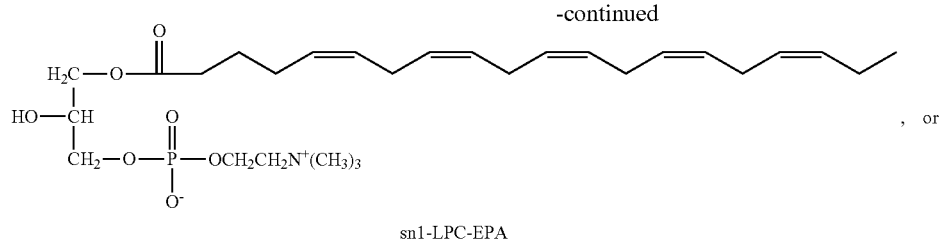

sn1-LPC-EPA

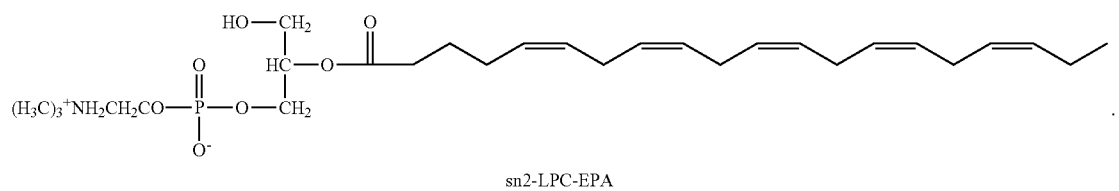

sn2-LPC-EPA

In certain embodiments, the lysophosphatidylcholine is obtained from an enzymatic conversion of phosphatidylcholine to lysophosphatidylcholine. The enzymatic conversion can be achieved by any suitable lipase enzyme and/or a phospholipase enzyme capable of hydrolyzing a phospholipid to release a fatty acid from the sn1 or sn2 position of the phosphatidylcholine. For example, the lipase enzyme can be phospholipase $A_1$ ($PLA_1$) or phospholipase $A_2$ ($PLA_2$). Exemplary methods for preparing lysophosphatidylcholine are set forth in Schemes A, B, and C.

Scheme A. Conversion of sn2 Fatty Acid to sn1 Fatty Acid.

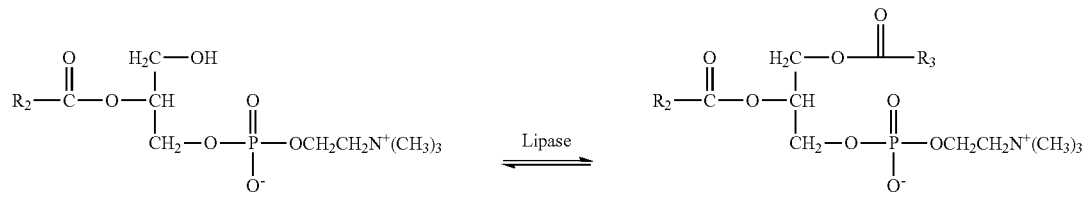

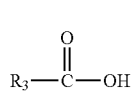

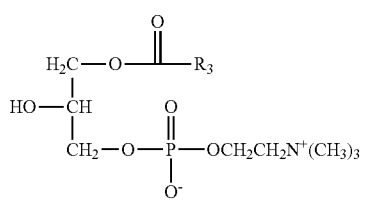

Scheme B. Fatty Acid Exchange on Phosphatidylcholine.
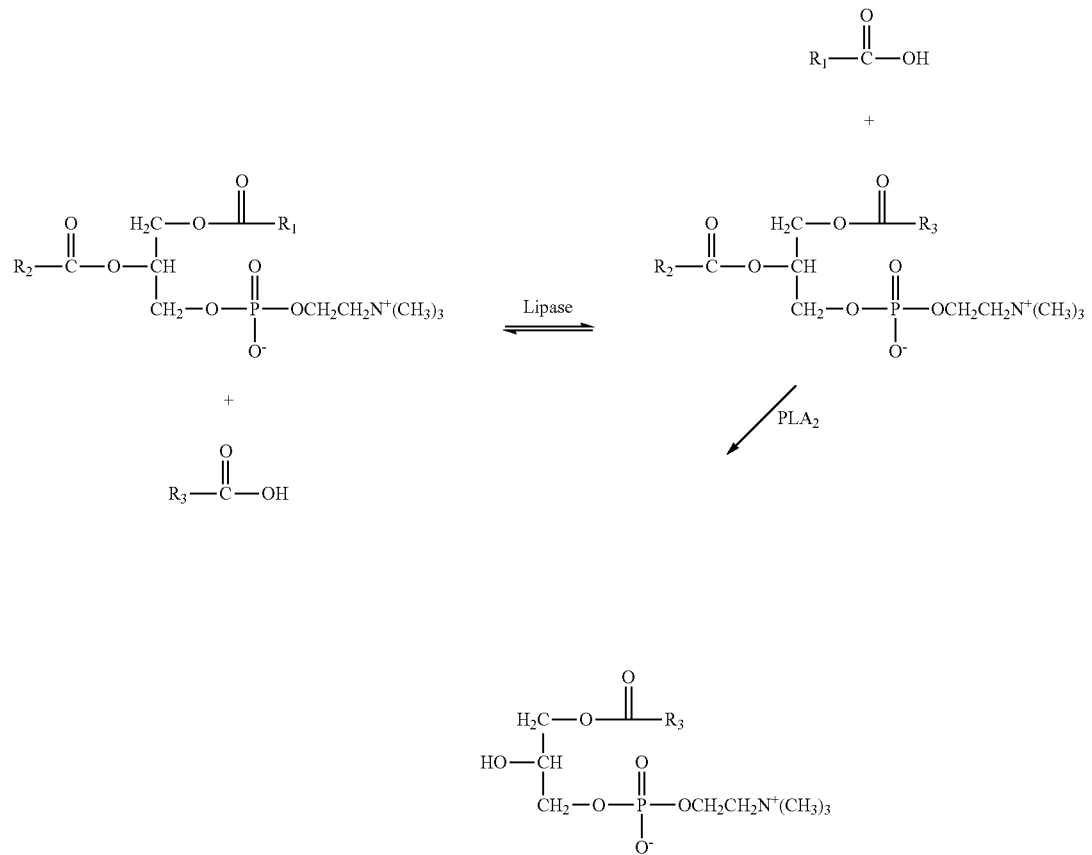
Scheme C. Acylglycerol Exchange on Phosphatidylcholine.
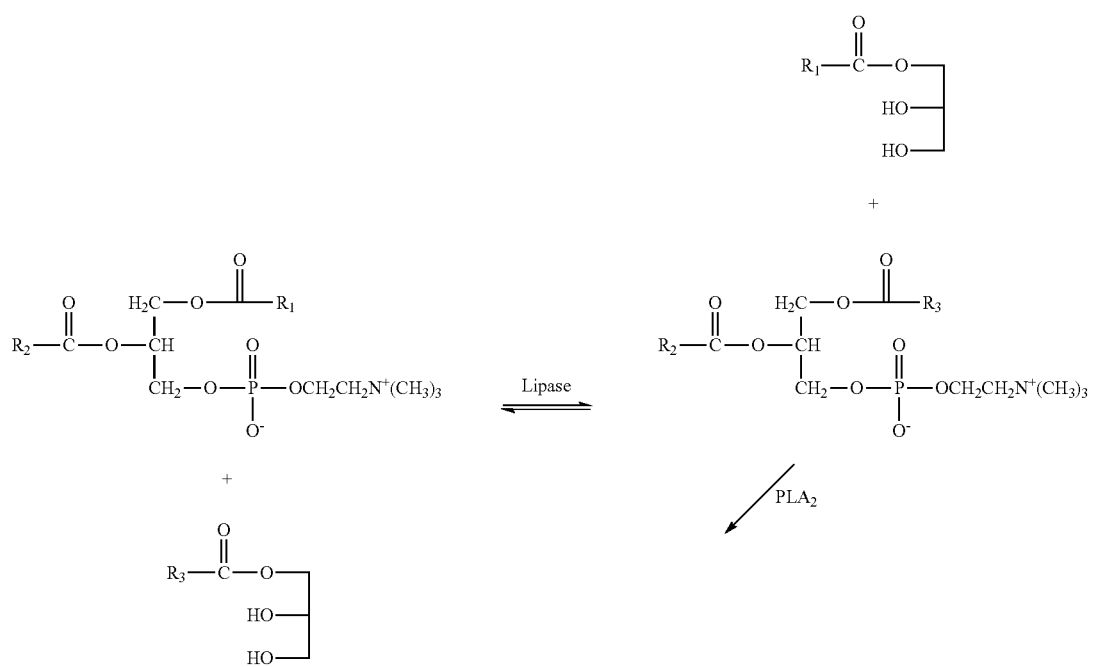

-continued

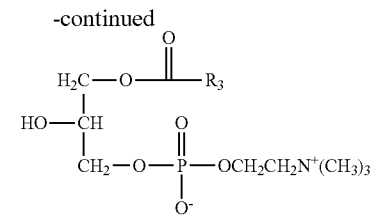

In each of Schemes A, B, and C, $R_1$, $R_2$, and $R_3$ are hydrocarbon chains of fatty acids. In some embodiments, $R_3$ of Schemes A, B, and C is docosahexaenoic acid (DHA) or eicosapentaenoic acid (EPA). It will be understood to those of ordinary skill in the art that $PLA_2$ of Schemes A, B, and C can be exchanged with $PLA_1$ to produce the corresponding sn2-LPC fatty acids.

In certain embodiments, the lipase enzyme and/or a phospholipase enzyme is an immobilized lipase enzyme and/or a phospholipase enzyme (e.g., Novozyme® 435, commercially available from Sigma-Aldrich, expressed in *Aspergillus niger*). The immobilized lipase enzyme and/or a phospholipase enzyme can be used in a batch reactor or a fixed bed reactor. Without wishing to be bound by any particular theory, an immobilized enzyme may allow for continuous production of lysophosphatidylcholine by utilizing a continuous-flow, fixed bed bioreactor. For example, acrylic lipase can be packed into a preparative chromatography column, equipped with a thermostat water jacket to maintain constant temperature of 50° C. Krill can be circulated through the column using an appropriate pump with optimized flow rate for 24 hours resulting in digestion of phosphatidylcholine.

Generally, the lysophosphatidylcholine (e.g., sn-1 or sn-2 LPC-DHA and/or sn-1 or sn-2 LPC-EPA) obtained from one of the techniques described herein results in a composition containing the lysophosphatidylcholine and at least one impurity. The at least one impurity can be considered any compound or mixture of compounds that are not the desired target lysophosphatidylcholine (e.g., sn-1 or sn-2 LPC-DHA and/or sn-1 or sn-2 LPC-EPA). For example, the at least one impurity can be any one of phospholipids, free fatty acids, triacylglycerols (TAGs), diacylglycerols (DAGs), monoacylglycerols (MAGs), glycerol, sterols, tocopherols, vitamin A, flavonoids, minerals, or mixtures thereof. In some embodiments, the lysophosphatidylcholine can be purified by a method comprising: passing a feedstock stream comprising the composition through at least one stationary phase to provide an eluate stream having a higher purity of the lysophosphatidylcholine than in the feedstock stream.

Embodiments of a method following principles of the present disclosure can comprise purifying and isolating lysophosphatidylcholine (e.g., sn-1 or sn-2 LPC-DHA and/or sn-1 or sn-2 LPC-EPA) using at least one chromatographic step (e.g., column chromatography). Any suitable adsorbent can be used for the chromatographic methods described herein. The adsorbent can be utilized in any suitable arrangement (e.g., single column chromatography, batch column chromatography, SMB chromatography, or a combination thereof). Embodiments of a method following principles of the present disclosure can comprise using more than one adsorbent and more than one arrangement to achieve the desired purity of lysophosphatidylcholine (e.g., sn-1 or sn-2 LPC-DHA and/or sn-1 or sn-2 LPC-EPA). In embodiments, a lysophosphatidylcholine (e.g., sn-1 or sn-2 LPC-DHA and/or sn-1 or sn-2 LPC-EPA) product having a total lysophosphatidylcholine (e.g., sn-1 or sn-2 LPC-DHA and/or sn-1 or sn-2 LPC-EPA) purity greater than 60 wt. % (e.g., greater than about 70 wt. %, greater than about 80 wt. %, greater than about 90 wt. %, greater than about 95 wt. %, greater than about 96 wt. %, greater than about 97 wt. %, greater than about 98 wt. %, or greater than about 99 wt. %) following drying (i.e., solvent removal) can be obtained. In some aspects, a lysophosphatidylcholine (e.g., sn-1 or sn-2 LPC-DHA and/or sn-1 or sn-2 LPC-EPA) recovery yield of greater than 25 wt. % (e.g., greater than about 35 wt. %, greater than about 45 wt. %, greater than about 50 wt. %, greater than about 60 wt. %, greater than about 70 wt. %, greater than about 80 wt. %, or greater than about 90 wt. %) following drying (i.e., solvent removal) can be obtained.

In various aspects, the disclosure relates to methods for purification and separation of lysophosphatidylcholine (e.g., sn-1 or sn-2 LPC-DHA and/or sn-1 or sn-2 LPC-EPA) from a phosphatidylcholine digestion of phosphatidylcholine obtained from natural sources such as fish oil, krill oil, egg, soybean, sunflower, or marine microalgae. Embodiments of a method following principles of the present disclosure can comprise employing chromatographic stationary phases and purification procedures for purifying and isolating lysophosphatidylcholine (e.g., sn-1 or sn-2 LPC-DHA and/or sn-1 or sn-2 LPC-EPA). In various embodiments, benefits of methods following principles of the disclosure include, but are not limited to, (i) increasing yield of lysophosphatidylcholine (e.g., sn-1 or sn-2 LPC-DHA and/or sn-1 or sn-2 LPC-EPA), (ii) increasing purity of lysophosphatidylcholine (e.g., sn-1 or sn-2 LPC-DHA and/or sn-1 or sn-2 LPC-EPA), and/or (iii) reducing the amount of phospholipids, free fatty acids, triacylglycerols (TAGs), diacylglycerols (DAGs), monoacylglycerols (MAGs), glycerol, sterols, tocopherols, vitamin A, flavonoids, or minerals.

In some aspects of the disclosure, column chromatography (e.g., SMB, batch, or single) can be utilized with any chromatographic stationary phases (e.g., a hydrophobic, crosslinked, polystyrene-divinylbenzene adsorbent, polydivinylbenzene adsorbent, macroporous polystyrene-divinylbenzene adsorbent, or macroporous polydivinylbenzene adsorbent) described herein to obtain an increased purity of lysophosphatidylcholine (e.g., sn-1 or sn-2 LPC-DHA and/or sn-1 or sn-2 LPC-EPA). The chromatographic stationary phases can be regenerated to obtain an increased yield of lysophosphatidylcholine (e.g., sn-1 or sn-2 LPC-DHA and/or sn-1 or sn-2 LPC-EPA), and potentially allow for reuse of the chromatographic stationary phases.

Typically, the stationary phase (i.e., adsorbent or resin) is contained in a container (e.g., a column). The terms "stationary phase," "adsorbent," "resin," and "chromatographic resin," can be used interchangeably. The container can be any suitable container. Generally the container is a column. The stationary phase (i.e., adsorbent or resin) can be in a single column, or in more than one column (e.g., two or more columns, three or more columns, four or more columns, five or more columns, six or more columns, seven or more columns, eight or more columns, nine or more columns, or ten or more columns). In some embodiments, the stationary phase (i.e., adsorbent) is in a single column. In some embodiments, the stationary phase (i.e., adsorbent or resin) is in more than one column (e.g., two columns, three columns, or four columns, etc.). In some embodiments, the methods described herein employ more than one (e.g., two, three, or four) stationary phases described herein, which are used in sequence or in parallel, arranged in any suitable configuration, and utilizing any suitable chromatograph method described herein.

The composition can be purified by any suitable chromatography method. For example, the composition can be purified by single column chromatography, batch column chromatography, or simulated moving bed (SMB) chromatography. In embodiments, single column chromatography comprises a purification process in which the composition is passed through a single stationary phase contained in a single container. In embodiments, batch column chromatography comprises a purification process in which the composition is passed through one or more stationary phases contained in more than one container. U.S. Pat. No. 2,985,589 describes a simulated moving bed (SMB) chromatography technique in which a chromatography system involving a separation tower is divided into a number of individual separation beds. These beds are connected in series, and the outlet at the bottom most bed is connected to a pump that returned flow in a continuous loop to the upper most bed. The inlet apparatus for each bed has a port connected to a downward flowing conduit. The conduits terminate in fittings attached to a rotary valve designed to control both ingress and egress of liquids into or from the inlets to each individual bed. The system is called Simulated Moving Bed (SMB) chromatography because the beds appear to be moving in a direction countercurrent to the direction of flow.

In some embodiments, the method comprises passing a composition through a SMB zone to provide a primary raffinate stream. The SMB zone comprises a plurality of adsorbent beds (e.g., columns comprising a stationary phase). The SMB zone can comprise any suitable number of adsorbent beds. For example, the SMB zone can comprise 2 or more adsorbent bed, e.g., 3 or more adsorbent beds, 4 or more adsorbent beds, 5 or more adsorbent beds, 6 or more adsorbent beds, 10 or more adsorbent beds, or 20 or more adsorbent beds. In some embodiments, the plurality of adsorbent beds are arranged in serial fluid communication such that fluid introduced at a top of any adsorbent bed (n) passes to the next highest adsorbent bed (n+1). In such embodiments, the method can further comprise advancing each adsorbent bed, such that adsorbent bed n+1 becomes adsorbent bed n after advancing, and adsorbent bed n prior to advancing becomes adsorbent bed n+x after advancing, wherein adsorbent bed n+x is the highest adsorbent bed in the serial fluid communication arrangement.

In some embodiments, the SMB zone comprises eight adsorbent beds. The eight adsorbent beds can be broken down into four zones referring to a desorption zone, a rectification zone, an adsorption zone, and a concentration zone. The adsorbent beds can be in any suitable arrangement (e.g., 2-2-2-2, 3-2-2-1, 2-3-2-1, 2-2-3-1, 1-3-3-1, 3-3-1-1, 3-1-3-1, or 2-2-3-1, etc.), wherein each number refers to one of the four zones. In certain embodiments, the SMB zone is in a 2-3-2-1 arrangement, wherein two adsorbent beds are operated in a desorption zone, three adsorbent beds are operated in a rectification zone, two adsorbent beds are operated in an adsorption zone, and one adsorbent bed is operated in a regeneration zone, respectively.

Any suitable stationary phase (i.e., adsorbent or resin) can be used in methods of the disclosure. Methods following principles of the disclosure can use normal-phase chromatography and/or reversed-phase chromatography. In embodiments, methods following principles of the present disclosure use normal-phase chromatography which comprises a suitable chromatography method using a non-polar mobile phase. As a result, polar molecules in the non-polar mobile phase tend to adsorb to the hydrophilic stationary phase, and hydrophobic molecules in the mobile phase will pass through the column and are eluted first. In embodiments, methods following principles of the present disclosure use reversed-phase chromatography which comprises a suitable chromatography method employing a polar (e.g., aqueous) mobile phase in. As a result, hydrophobic molecules in the polar mobile phase tend to adsorb to the hydrophobic stationary phase, and hydrophilic molecules in the mobile phase will pass through the column and are eluted first. In some embodiments, methods following principles of the present disclosure use both normal-phase chromatography and reversed-phase chromatography, which are employed in tandem (e.g., in series).

In preferred embodiments, methods following principles of the present disclosure use a hydrophobic adsorbent (i.e., reversed-phase chromatography) such as a divinylbenzene-based adsorbent. As used herein, the phrase "hydrophobic divinylbenzene-based adsorbent" can refer to any polystyrene-divinylbenzene adsorbent, polydivinylbenzene adsorbent, macroporous polystyrene-divinylbenzene adsorbent, or macroporous polydivinylbenzene adsorbent having an average particle diameter of 20 microns to 600 microns, an average surface area of 300 m$^2$/g to 900 m$^2$/g, an average porosity of 75 Å to 1000 Å, an average water content of 35% to 80%, an average bulk density of 0.45 g/mL to 0.9 g/mL, or any combination thereof. In certain embodiments, the hydrophobic adsorbent comprises a polystyrene-divinylbenzene adsorbent, a polydivinylbenzene adsorbent, or a combination thereof.

The stationary phase (e.g., hydrophobic adsorbent) can have any suitable average particle diameter. For example, the stationary phase (e.g., hydrophobic adsorbent) can have an average particle diameter of about 20 µm to about 600 µm, about 20 µm to about 500 µm, about 20 µm to about 400 µm, about 20 µm to about 200 µm, about 50 µm to about 600 µm, about 50 µm to about 400 µm, about 50 µm to about 300 µm, or about 50 µm to about 200 µm. In some embodiments, the hydrophobic divinylbenzene-based adsorbent has an average particle diameter of from 20 microns to 300 microns (e.g., about 20 microns to about 250 microns, about 20 microns to about 225 microns, or about 20 microns to about 200 microns). In certain embodiments, the hydrophobic divinylbenzene-based adsorbent has an average particle diameter of from 20 microns to 250 microns or from 20 microns to 225 microns. In preferred embodiments, the stationary phase (e.g., hydrophobic adsorbent) has an average particle diameter of about 75 µm to about 200 µm.

The stationary phase (e.g., hydrophobic adsorbent) can have any suitable average porosity. For example, the stationary phase (e.g., hydrophobic adsorbent) can have an average porosity of about 75 Å to about 1000 Å, about 100 Å to about 1000 Å, about 100 Å to about 900 Å, about 100 Å to about 800 Å, about 100 Å to about 700 Å, about 100 Å to about 600 Å, about 100 Å to about 500 Å, about 200 Å to about 1000 Å, about 200 Å to about 900 Å, about 200 Å to about 800 Å, about 200 Å to about 700 Å, about 200 Å to about 600 Å, about 200 Å to about 500 Å, about 300 Å to about 1000 Å, about 300 Å to about 900 Å, about 300

Å to about 800 Å, about 300 Å to about 700 Å, about 300 Å to about 600 Å, or about 300 Å to about 500 Å. In preferred embodiments, the stationary phase (e.g., hydrophobic adsorbent) has an average porosity of about 300 Å to about 500 Å.

The stationary phase (e.g., hydrophobic adsorbent) can have any suitable average surface area. For example, the stationary phase (e.g., hydrophobic adsorbent) can have an average surface area of at least about 300 m$^2$/g, at least about 400 m$^2$/g, at least about 500 m$^2$/g, or at least about 600 m$^2$/g. In preferred embodiments, the stationary phase (e.g., hydrophobic adsorbent) has an average surface area of at least about 600 m$^2$/g.

The stationary phase (e.g., hydrophobic adsorbent) can have any suitable average water content. For example, the stationary phase (e.g., hydrophobic adsorbent) can have an average water content of about 35% to about 80%, about 35% to about 75%, about 35% to about 70%, about 35% to about 65%, 45% to about 80%, about 45% to about 75%, about 45% to about 70%, about 45% to about 65%, 55% to about 80%, about 55% to about 75%, about 55% to about 70%, about 55% to about 65%, about 60% to about 80%, about 60% to about 75%, about 60% to about 70%, about 65% to about 80%, or about 65% to about 75%. In preferred embodiments, the stationary phase (e.g., hydrophobic adsorbent) has an average water content of about 35% to about 70%.

The stationary phase (e.g., hydrophobic adsorbent) can have any suitable average bulk density. For example, the stationary phase (e.g., hydrophobic adsorbent) can have an average bulk density of about 0.45 g/mL to about 0.9 g/mL, about 0.45 g/mL to about 0.8 g/mL, about 0.45 g/mL to about 0.7 g/mL, about 0.45 g/mL to about 0.6 g/mL, about 0.5 g/mL to about 0.9 g/mL, about 0.5 g/mL to about 0.8 g/mL, about 0.5 g/mL to about 0.7 g/mL, about 0.5 g/mL to about 0.6 g/mL, about 0.55 g/mL to about 0.9 g/mL, about 0.55 g/mL to about 0.8 g/mL, about 0.55 g/mL to about 0.7 g/mL, or about 0.55 g/mL to about 0.6 g/mL.

In some embodiments, the stationary phase comprises a hydrophobic polystyrene-divinylbenzene adsorbent. The hydrophobic polystyrene-divinylbenzene adsorbent can have an average particle diameter of from about 250 microns to about 600 microns (e.g., about 250 microns to about 500 microns, about 250 microns to about 400 microns, about 250 microns to about 300 microns, about 300 microns to about 600 microns, about 400 microns to about 600 microns, about 500 microns to about 600 microns, or about 300 microns to about 500 microns). Additionally, or alternatively, the hydrophobic polystyrene-divinylbenzene adsorbent can have an average bulk density of from about 0.6 g/mL to about 0.9 g/mL (e.g., about 0.6 g/mL, about 0.65 g/mL, about 0.7 g/mL, about 0.75 g/mL, about 0.8 g/mL, about 0.85 g/mL, or about 0.9 g/mL), an average water content of from about 35% to about 65% (e.g., about 60%), or a combination thereof.

In some embodiments, the stationary phase comprises a hydrophobic divinylbenzene-based adsorbent (e.g., a polystyrene-divinylbenzene adsorbent, a polydivinylbenzene adsorbent, a macroporous polystyrene-divinylbenzene adsorbent, or a macroporous polydivinylbenzene adsorbent) having an average particle diameter range from 60 microns to 300 microns (e.g., about 60 microns to about 250 microns, about 60 microns to about 225 microns, or about 60 microns to about 200 microns). Alternatively, or additionally, the hydrophobic divinylbenzene-based adsorbent can have an average bulk density of from about 0.6 g/mL to about 0.9 g/mL (e.g., about 0.6 g/mL, about 0.65 g/mL, about 0.7 g/mL, about 0.75 g/mL, about 0.8 g/mL, about 0.85 g/mL, or about 0.9 g/mL) or from about 0.65 g/mL to about 0.7 g/mL, an average water content of from about 35% to about 80% (e.g., about 55% to about 80%, about 55% to about 70%, about 55% to about 67%, about 55% to about 65%, or about 65% to about 80%), an average pore size of from about 75 Å to 550 Å (e.g., about 100 Å to about 550 Å, about 200 Å to about 550 Å, about 300 Å to about 550 Å, about 100 Å to about 500 Å, about 200 Å to about 500 Å, about 300 Å to about 500 Å, about 100 Å to about 400 Å, about 200 Å to about 400 Å, or about 300 Å to about 400 Å), an average surface area of from about 450 m$^2$/g to about 900 m$^2$/g (e.g., about 450 m$^2$/g to about 600 m$^2$/g, about 550 m$^2$/g to about 600 m$^2$/g, about 560 m$^2$/g to about 600 m$^2$/g, or about 560 m$^2$/g to about 590 m$^2$/g, about 550 m$^2$/g to about 900 m$^2$/g, about 600 m$^2$/g to about 900 m$^2$/g, about 600 m$^2$/g to about 800 m$^2$/g, or about 600 m$^2$/g to about 700 m$^2$/g), a minimum surface area of from about 450 m$^2$/g to about 900 m$^2$/g (e.g., about 450 m$^2$/g to about 600 m$^2$/g, about 550 m$^2$/g to about 600 m$^2$/g, about 560 m$^2$/g to about 600 m$^2$/g, or about 560 m$^2$/g to about 590 m$^2$/g), or a combination thereof.

In some embodiments, the stationary phase comprises a hydrophobic divinylbenzene-based adsorbent (e.g., a polystyrene-divinylbenzene adsorbent, a polydivinylbenzene adsorbent, a macroporous polystyrene-divinylbenzene adsorbent, or a macroporous polydivinylbenzene adsorbent) having an average particle diameter range from 20 microns to 200 microns (e.g., about 20 microns to about 160 microns, about 20 microns to about 120 microns, about 20 microns to about 100 microns, about 20 microns to about 80 microns, about 20 microns to about 60 microns, or about 60 microns to about 100 microns). Alternatively, or additionally, the hydrophobic divinylbenzene-based adsorbent can have an average bulk density of from about 0.45 g/mL to about 0.9 g/mL (e.g., about 0.45 g/mL, about 0.5 g/mL, about 0.55 g/mL, about 0.65 g/mL, about 0.75 g/mL, about 0.8 g/mL, about 0.85 g/mL, or about 0.9 g/mL) or from about 0.45 g/mL to about 0.7 g/mL, an average water content of from about 35% to about 80% (e.g., about 55% to about 80%, about 55% to about 70%, about 55% to about 67%, about 55% to about 65%, or about 65% to about 80%), an average pore size of from about 75 Å to 550 Å (e.g., about 100 Å to about 550 Å, about 200 Å to about 550 Å, about 300 Å to about 550 Å, about 100 Å to about 500 Å, about 200 Å to about 500 Å, about 300 Å to about 500 Å, about 100 Å to about 400 Å, about 200 Å to about 400 Å, or about 300 Å to about 400 Å), an average surface area of from about 450 m$^2$/g to about 900 m$^2$/g (e.g., about 450 m$^2$/g to about 600 m$^2$/g, about 550 m$^2$/g to about 600 m$^2$/g, about 560 m$^2$/g to about 600 m$^2$/g, or about 560 m$^2$/g to about 590 m$^2$/g, about 550 m$^2$/g to about 900 m$^2$/g, about 600 m$^2$/g to about 900 m$^2$/g, about 600 m$^2$/g to about 800 m$^2$/g, or about 600 m$^2$/g to about 700 m$^2$/g), a minimum surface area of from about 450 m$^2$/g to about 900 m$^2$/g (e.g., about 550 m$^2$/g to about 900 m$^2$/g, about 600 m$^2$/g to about 900 m$^2$/g, about 600 m$^2$/g to about 800 m$^2$/g, or about 600 m$^2$/g to about 700 m$^2$/g), or a combination thereof.

In some embodiments, the hydrophobic divinylbenzene-based adsorbent (e.g., the polystyrene-divinylbenzene adsorbent, polydivinylbenzene adsorbent, macroporous polystyrene-divinylbenzene adsorbent, or macroporous polydivinylbenzene adsorbent) has an average particle diameter of from 250 microns to about 600 microns (e.g., about 300 microns to about 600 microns, about 400 microns to about 600 microns, about 500 microns to about 600 microns, or about 300 microns to about 500 microns average bulk density of from about 0.6 g/mL to about 0.9 g/mL, and an average water content of from about 35% to about 70% (e.g., about 35% to about 67%, about 55% to about 70%/o, or about 55% to about 67%).

In some embodiments, the hydrophobic divinylbenzene-based adsorbent (e.g., the polystyrene-divinylbenzene adsorbent, polydivinylbenzene adsorbent, macroporous polystyrene-divinylbenzene adsorbent, or macroporous polydivinylbenzene adsorbent) has an average particle diameter of from 20 microns to 300 microns (e.g., about 20 microns to about 250 microns, about 20 microns to about 225 microns, or about 20 microns to about 200 microns), an average bulk density of from about 0.45 g/mL to about 0.7 g/mL, an average water content of from about 35% to about 70% (e.g., about 35% to about 67%, about 55% to about 70%, or about 55% to about 67%), and an average surface area of from about 550 $m^2/g$ to about 600 $m^2/g$.

In some embodiments, the hydrophobic divinylbenzene-based adsorbent (e.g., the polystyrene-divinylbenzene adsorbent, polydivinylbenzene adsorbent, macroporous polystyrene-divinylbenzene adsorbent, or macroporous polydivinylbenzene adsorbent) has an average particle diameter range from 20 microns to 200 microns (e.g., about 20 microns to about 160 microns, about 20 microns to about 120 microns, about 20 microns to about 100 microns, about 20 microns to about 80 microns, or about 20 microns to about 60 microns), an average bulk density of from about 0.65 g/mL to about 0.7 g/mL, an average water content of from about 35% to about 70% (e.g., about 35% to about 67%, about 55% to about 70%, or about 55% to about 67%), and an average surface area of from about 550 $m^2/g$ to about 600 $m^2/g$.

In some embodiments, the hydrophobic divinylbenzene-based adsorbent (e.g., the polystyrene-divinylbenzene adsorbent, polydivinylbenzene adsorbent, macroporous polystyrene-divinylbenzene adsorbent, or macroporous polydivinylbenzene adsorbent) has an average particle diameter range from about 20 microns to about 200 microns (e.g., about 20 microns to about 60 microns or about 60 microns to about 100 microns), an average pore size of from about 300 Å to 500 Å, an average water content of from about 35% to about 80% (e.g., about 55% to about 80%), and an average surface area of from about 550 $m^2/g$ to about 650 $m^2/g$.

In some embodiments, the hydrophobic divinylbenzene-based adsorbent (e.g., the polystyrene-divinylbenzene adsorbent, polydivinylbenzene adsorbent, macroporous polystyrene-divinylbenzene adsorbent, or macroporous polydivinylbenzene adsorbent) has an average particle diameter range from about 20 microns to about 200 microns (e.g., e.g., about 20 microns to about 120 microns, about 20 microns to about 60 microns or about 60 microns to about 120 microns), an average pore size of from about 200 Å to about 400 Å, and an average surface area of from about 600 $m^2/g$ to about 800 $m^2/g$.

In some embodiments, the hydrophobic divinylbenzene-based adsorbent (e.g., the polystyrene-divinylbenzene adsorbent, polydivinylbenzene adsorbent, macroporous polystyrene-divinylbenzene adsorbent, or macroporous polydivinylbenzene adsorbent) has an average particle diameter range from 60 microns to 300 microns (e.g., about 60 microns to about 250 microns, about 60 microns to about 225 microns, or about 60 microns to about 200 microns), an average pore size of from about 200 Å to about 400 Å, and an average surface area of from about 600 $m^2/g$ to about 800 $m^2/g$.

In some embodiments, the stationary phase is a hydrophobic, crosslinked, porous polydivinylbenzene adsorbent having an average particle diameter of about 75 μm to about 200 μm, an average porosity of about 300 Å to about 500 Å, and surface area of at least about 600 $m^2/g$.

In some preferred embodiments, the stationary phase is a Chromalite® resin (e.g., PCG1200C, PCG1200F, or PCG1200M) commercially available from Purolite® Life Sciences. In some preferred embodiments, the stationary phase is an Amberchrom® resin (e.g., CG300S, CG300M, or CG300C) commercially available from MilliporeSigma. In some preferred embodiments, the stationary phase is a Diaion® resin (e.g., HP20, HP20S, or HP20SS) commercially available from Mitsubishi Chemical Corporation. In some preferred embodiments, the stationary phase is a Sepabeads' resin (e.g., SP207, SP207SS), commercially available from Mitsubishi Chemical Corporation. In certain embodiments, more than one of the foregoing resins is used.

In embodiments, methods following principles of the present disclosure can utilize a solvent (i.e., "desorbent" or "mobile phase") in the feedstock stream to elute the lysophosphatidylcholine (e.g., sn-1 or sn-2 LPC-DHA and/or sn-1 or sn-2 LPC-EPA) from the stationary phase. In some embodiments, the combination of the lysophosphatidylcholine (e.g., sn-1 or sn-2 LPC-DHA and/or sn-1 or sn-2 LPC-EPA), the at least one impurity, and the solvent (i.e., "desorbent" or "mobile phase") can be considered the feedstock stream. The solvent can be any suitable mobile phase capable of eluting the lysophosphatidylcholine (e.g., sn-1 or sn-2 LPC-DHA and/or sn-1 or sn-2 LPC-EPA). For example, the solvent can comprise water, ethanol, acetone, ethyl acetate, acetonitrile, pentanes, hexanes, heptanes, methanol, propanol, or a combination thereof. In certain embodiments, the solvent is selected from water, ethanol, acetone, ethyl acetate, acetonitrile, methanol, propanol, and a combination thereof. For the purposes of this disclosure, water, ethanol, acetone, ethyl acetate, acetonitrile, methanol, and propanol can be considered particularly useful for elution from hydrophobic adsorbents. In preferred embodiments, the feedstock stream comprises ethanol.

Embodiments of a method following principles of the present disclosure can use a solvent (i.e., "desorbent" or "mobile phase") comprising a mixture of ethanol (e.g., food grade ethanol) and water (e.g., deionized water), or in other words, an ethanolic mixture. In embodiments, the solvent has a ratio of ethanol to water in a range from about 50 parts ethanol (e.g., Food grade ethanol—200 Proof) to about 50 parts water to about 95 parts ethanol to about 5 parts water (i.e., a ratio of ethanol to water in a range from about 50:50 to about 95:5). In some embodiments, the solvent has a ratio of ethanol to water in a range from about 60 parts ethanol to about 40 parts water to about 95 parts ethanol to about 5 parts water. In embodiments, the solvent has a ratio of ethanol to water of equal to or greater than 50 parts ethanol to 50 parts water. In embodiments, the solvent used in the methods of the present disclosure has a ratio of ethanol to water of about 50:50, about 55:45, about 60:40, about 65:35, about 70:30, about 75:25, about 80:20, about 85:15, about 90:10, or about 95:5.

It will be understood to those of ordinary skill in the art that solvent can be removed (i.e., the composition can be concentrated) and/or added to any composition. The solvent can be removed or added for any suitable reason. For example, solvent can be removed or added to (i) change the polarity of the composition, (ii) obtain a dry sample of the composition, (iii) isolate the final product, or (iv) increase or decrease the loading amount for column chromatography.

In some embodiments, the method further comprises drying the eluate stream to produce a purified composition comprising lysophosphatidylcholine. The eluate stream can be dried (i.e., the solvent can be removed) by any suitable method. For example, the solvent can be removed by evaporation (e.g., under reduced pressure, elevated temperature, or a combination thereof), membrane permeation (e.g., nano-filtration), or a combination thereof.

In some embodiments, the methods described herein provide an isolated yield (i.e., a percent recovery) after removal of solvent of at least about 25% or more (e.g., at least about 35% or more, at least about 45% or more, at least about 50% or more, at least about 55% or more, at least about 60% or more, at least about 65% or more, at least about 70% or more, at least about 80% or more, at least about 85% or more, at least about 90% or more, or at least about 95% or more) of the lysophosphatidylcholine (e.g., sn-1 or sn-2 LPC-DHA and/or sn-1 or sn-2 LPC-EPA). In preferred embodiments, the methods described herein provide an isolated yield of from about 35% to about 100% (e.g., about 50% to about 100%, about 75% to about 100%, about 75% to about 90%, about 75% to about 85%, about 80% to about 100%, about 80% to about 90%, about 85% to about 100%, or about 85% to about 90%) of the lysophosphatidylcholine (e.g., sn-1 or sn-2 LPC-DHA and/or sn-1 or sn-2 LPC-EPA).

In some embodiments, the methods described herein provide a purified composition comprising lysophosphatidylcholine (e.g., sn-1 or sn-2 LPC-DHA and/or sn-1 or sn-2 LPC-EPA) having a total lysophosphatidylcholine purity greater than about 60 wt. % (e.g., greater than about 70 wt. %, greater than about 80 wt. %, greater than about 85 wt. %, greater than about 90 wt. %, greater than about 95 wt. %, greater than about 96 wt. %, greater than about 97 wt. %, greater than about 98 wt. %, greater than about 99 wt. %, or greater than about 99.9 wt. %) following removal of solvent.

In some aspects, the present disclosure provides a purified composition comprising lysophosphatidylcholine (e.g., sn-1 or sn-2 LPC-DHA and/or sn-1 or sn-2 LPC-EPA) in an amount greater than about 60 wt. % (e.g., greater than about 70 wt. %, greater than about 80 wt. %, greater than about 85 wt. %, greater than about 90 wt. %, greater than about 95 wt. %, greater than about 96 wt. %, greater than about 97 wt. %, greater than about 98 wt. %, greater than about 99 wt. %, or greater than about 99.9 wt. %).

In some embodiments, the purified composition comprises both LPC-DHA and LPC-EPA. The purified composition can comprise any suitable ratio of LPC-DHA and LPC-EPA. For example, the purified composition can comprise LPC-DHA and LPC-EPA in a ratio of from about 1:10 to about 10:1, for example, from about 1:5 to about 5:1, or from about 1:3 to about 3:1. In such embodiments, the purified composition comprises a sum total of LPC-EPA and LPC-DHA in an amount greater than about 60 wt. % (e.g., greater than about 70 wt. %, greater than about 80 wt. %, greater than about 85 wt. %, greater than about 90 wt. %, greater than about 95 wt. %, greater than about 96 wt. %, greater than about 97 wt. %, greater than about 98 wt. %, greater than about 99 wt. %, or greater than about 99.9 wt. %). In certain embodiments, the purified composition comprises at least twice as much LPC-EPA as LPC-DHA.

In some embodiments, the purified composition comprises LPC-DHA and not LPC-EPA. In such embodiments, the purified composition comprises LPC-DHA in an amount greater than about 60 wt. % (e.g., greater than about 70 wt. %, greater than about 80 wt. %, greater than about 85 wt. %, greater than about 90 wt. %, greater than about 95 wt. %, greater than about 96 wt. %, greater than about 97 wt. %, greater than about 98 wt. %, greater than about 99 wt. %, or greater than about 99.9 wt. %).

In some embodiments, the purified composition comprises LPC-EPA and not LPC-DHA. In such embodiments, the purified composition comprises LPC-EPA in an amount greater than about 60 wt. % (e.g., greater than about 70 wt. %, greater than about 80 wt. %, greater than about 85 wt. %, greater than about 90 wt. %, greater than about 95 wt. %, greater than about 96 wt. %, greater than about 97 wt. %, greater than about 98 wt. %, greater than about 99 wt. %, or greater than about 99.9 wt. %).

Figure 11:
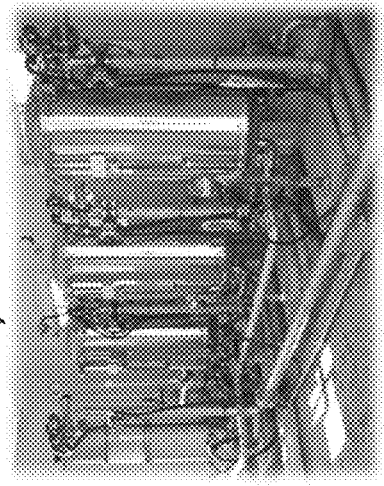
FIG. 11 is a flow diagram of the process to produce high purity LPC-EPA and LPC-DHA, which shows the step of converting krill oil to hydrolyzed krill oil using enzyme reactors.
Figure 11:
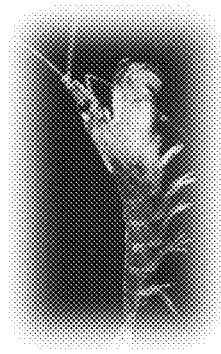
Figure 11:
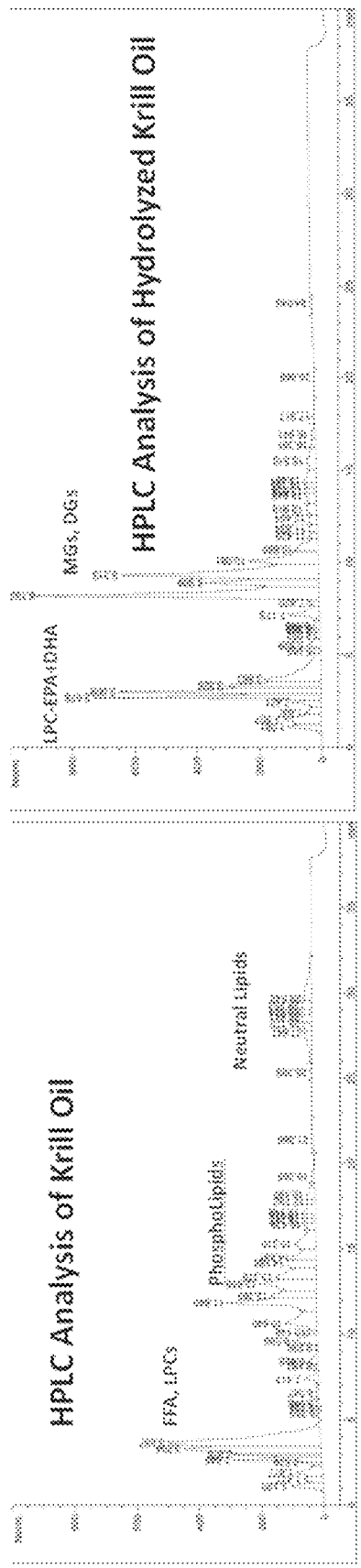
Figure 12:
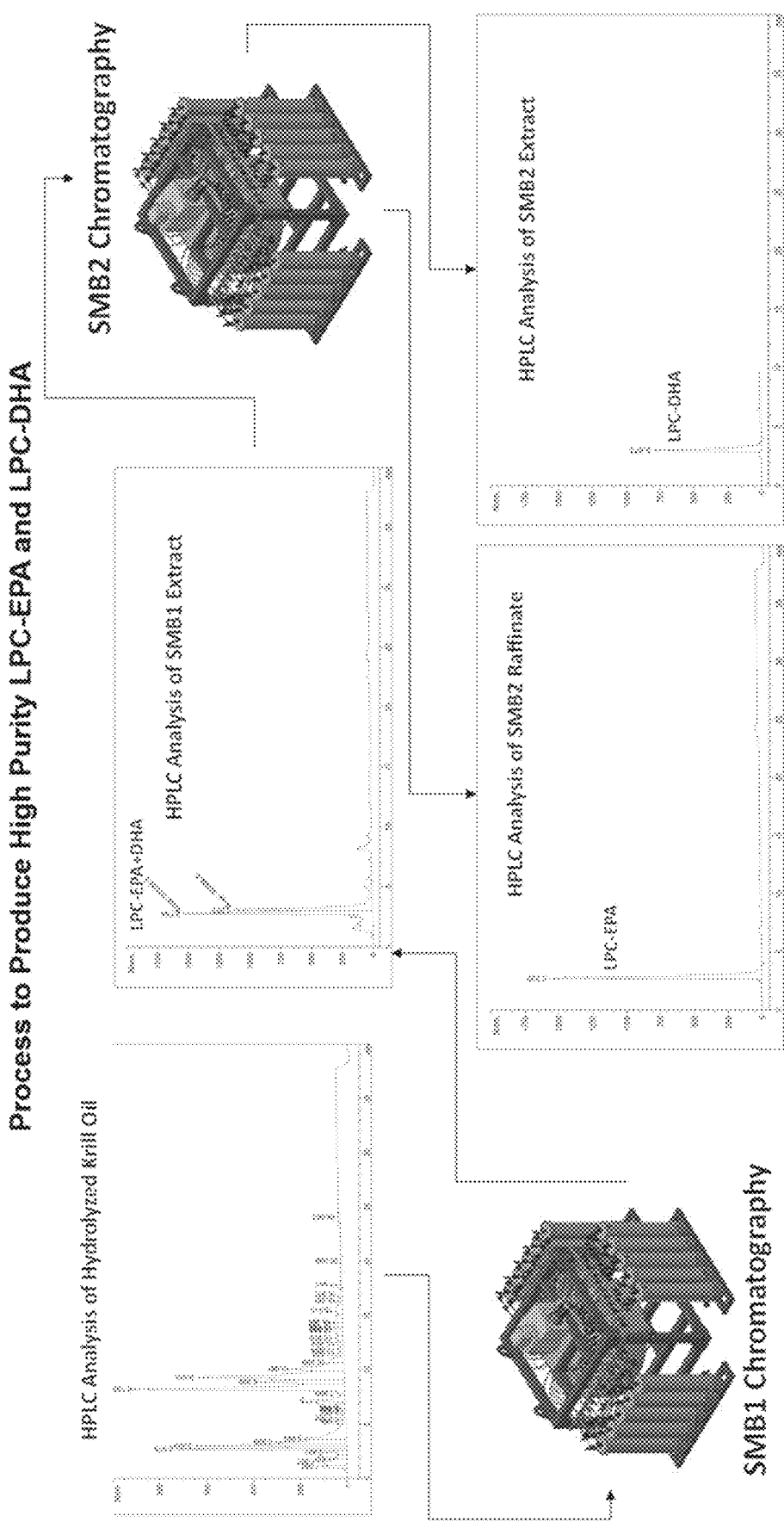
FIG. 12 is a flow diagram of the process to produce high purity LPC-EPA and LPC-DHA, which shows the steps of (i) purifying the hydrolyzed krill oil using a first SMB chromatography to produce a mixture of LPC-EPA and LPC-DHA and (ii) purifying the mixture of LPC-EPA and LPC-DHA using a second SMB chromatography to produce pure LPC-EPA and pure LPC-DHA.

In an illustrative aspect of the invention, krill oil can be converted to hydrolyzed krill oil using an enzyme reactor, as described herein, and as shown in FIG. 11. An exemplary procedure for converting krill oil into hydrolyzed krill oil using an enzyme reactor is provided in Example 1. The hydrolyzed krill oil can be purified using a first SMB chromatography step to produce a purified mixture of LPC-EPA and LPC-DHA, as described herein, and as shown in FIG. 12. An exemplary procedure for purifying the hydrolyzed krill oil by a first SMB chromatography step is provided in Example 2. The purified mixture of LPC-EPA and LPC-DHA can be further purified using a second SMB chromatography step to produce pure LPC-EPA and pure LPC-DHA, as described herein, and as shown in FIG. 12. An exemplary procedure for purifying the purified mixture of LPC-EPA and LPC-DHA using a second SMB chromatography step is provided in Example 4. All other features of this illustrative, exemplary embodiment of the invention will be readily apparent from the disclosure provided herein, and other embodiments of a process following principles of the present disclosure will be readily apparent to one skilled in the art.

In some aspects, the present disclosure provides a dietary supplement (i.e., nutraceutical) or a pharmaceutical composition comprising the purified composition prepared by any of the methods disclosed herein. The dietary supplement (i.e., nutraceutical) or a pharmaceutical composition can be an oil, a powder, a hard tablet, a capsulated powder, a capsulated gel, a soft gel (e.g., chewable), a liquid (e.g., drink), etc. In certain embodiments, the dietary supplement (i.e., nutraceutical) or a pharmaceutical composition comprising lysophosphatidylcholine (e.g., sn-1 or sn-2 LPC-DHA and/or sn-1 or sn-2 LPC-EPA) is in the form of a soft gel chewable.

The dietary supplement (i.e., nutraceutical) or pharmaceutical composition can comprise any suitable amount of lysophosphatidylcholine (e.g., sn-1 or sn-2 LPC-DHA and/or sn-1 or sn-2 LPC-EPA). The dietary supplement (i.e., nutraceutical) or pharmaceutical composition can comprise from about 1 mg to about 10 g of the lysophosphatidylcholine (e.g., sn-1 or sn-2 LPC-DHA and/or sn-1 or sn-2 LPC-EPA), for example, from about 1 mg to about 5 g, from about 1 mg to about 1 g, from about 10 mg to about 1 g, from about 1 mg to about 500 mg, from about 10 mg to about 500 mg, from about 1 mg to about 100 mg, from about 10 mg to about 100 mg, from about 1 mg to about 50 mg, or from about 10 mg to about 50 mg of the lysophosphatidylcholine (e.g., sn-1 or sn-2 LPC-DHA and/or sn-1 or sn-2 LPC-EPA).

The dietary supplement (i.e., nutraceutical) or pharmaceutical composition can further comprise one or more pharmaceutically acceptable excipients. Suitable excipients and the amounts to use may be readily determined under the direction of one of ordinary skill in the art based upon experience and consideration of standard procedures and reference works in the field, e.g., sweetening agents, dyes, flavoring agents, and preservatives.

In some aspects, the present disclosure provides a method of treating and/or preventing a neurological disease or disorder comprising: administering an effective amount of a purified composition, a dietary supplement, or a pharmaceutical composition described herein. As used herein, an "effective amount" refers to an amount effective to increase docosahexaenoic acid (DHA), eicosapentaenoic acid (EPA), or a combination thereof in the brain of the subject. In some embodiments, the neurological disease or disorder is depression, dementia, or a traumatic brain injury. In some embodiments, the neurological disease or disorder is Alzheimer's disease or Parkinson's disease.

In certain aspects, the present disclosure provides a method of treating and/or preventing Alzheimer's disease (AD) and related dementia (ADRD) comprising: administering an effective amount of a purified composition, a dietary supplement, or a pharmaceutical composition described herein.

EMBODIMENTS

Principles of the present disclosure are incorporated in the following embodiments:

Embodiment 1. A method of purifying a lysophosphatidylcholine from a composition containing the lysophosphatidylcholine and at least one impurity, the method comprising:
passing a feedstock stream comprising the composition through at least one stationary phase to provide an eluate stream having a higher purity of the lysophosphatidylcholine than in the feedstock stream.

Embodiment 2. The method of Embodiment 1, wherein the lysophosphatidylcholine is lysophosphatidylcholine-docosahexaenoic acid (LPC-DHA), lysophophatidylcholine-eicosapentaenoic acid (LPC-EPA), or a combination thereof.

Embodiment 3. The method of Embodiment 1 or Embodiment 2, wherein the lysophosphatidylcholine is a combination of lysophosphatidylcholine-docosahexaenoic acid (LPC-DHA) and lysophophatidylcholine-eicosapentaenoic acid (LPC-EPA).

Embodiment 4. The method of Embodiment 1 or Embodiment 2, wherein the lysophosphatidylcholine is lysophosphatidylcholine-docosahexaenoic acid (LPC-DHA).

Embodiment 5. The method of Embodiment 3 or Embodiment 4, wherein the LPC-DHA is sn1-LPC-DHA.

Embodiment 6. The method of Embodiment 3 or Embodiment 4, wherein the LPC-DHA is sn2-LPC-DHA.

Embodiment 7. The method of Embodiment 1 or Embodiment 2, wherein the lysophosphatidylcholine is lysophophatidylcholine-eicosapentaenoic acid (LPC-EPA).

Embodiment 8. The method of Embodiment 3 or Embodiment 7, wherein the LPC-EPA is sn1-LPC-EPA.

Embodiment 9. The method of Embodiment 3 or Embodiment 7, wherein the LPC-EPA is sn2-LPC-EPA.

Embodiment 10. The method of any one of Embodiments 1-9, wherein the stationary phase comprises a hydrophobic adsorbent.

Embodiment 11. The method of Embodiment 10, wherein the hydrophobic adsorbent is a divinylbenzene-based adsorbent having:
(i) an average particle diameter of 20 microns to 600 microns,
(ii) an average surface area of 300 $m^2/g$ to 900 $m^2/g$,
(iii) an average porosity of 75 Å to 1000 Å,
(iv) an average water content of 35% to 80%,
(v) an average bulk density of 0.45 g/mL to 0.9 g/mL, or
(vi) any combination thereof.

Embodiment 12. The method of Embodiment 10 or Embodiment 11, wherein the hydrophobic adsorbent comprises a polystyrene-divinylbenzene adsorbent, a polydivinylbenzene adsorbent, or a combination thereof.

Embodiment 13. The method of any one of Embodiments 10-12, wherein the hydrophobic adsorbent has an average particle diameter of 20 microns to 600 microns.

Embodiment 14. The method of any one of Embodiments 10-13, wherein the hydrophobic adsorbent has an average particle diameter of 20 μm to 200 μm.

Embodiment 15. The method of any one of Embodiments 10-14, wherein the hydrophobic adsorbent has an average surface area of 300 $m^2/g$ to 900 $m^2/g$.

Embodiment 16. The method of any one of Embodiments 10-15, wherein the hydrophobic adsorbent has an average surface area of 300 $m^2/g$ to 600 $m^2/g$.

Embodiment 17. The method of any one of Embodiments 10-16, wherein the hydrophobic adsorbent has an average porosity of 75 Å to 1000 Å.

Embodiment 18. The method of any one of Embodiments 10-17, wherein the hydrophobic adsorbent has an average porosity of 300 Å to 500 Å.

Embodiment 19. The method of any one of Embodiments 1-18, wherein said at least one impurity comprises at least one of phospholipids, free fatty acids, triacylglycerols (TAGs), diacylglycerols (DAGs), monoacylglycerols (MAGs), glycerol, sterols, tocopherols, vitamin A, flavonoids, minerals, and mixtures thereof.

Embodiment 20. The method of any one of Embodiments 1-19, wherein the at least one stationary phase is disposed in a single column or more than one column in series.

Embodiment 21. The method of any one of Embodiments 1-19, wherein the at least one stationary phase is one stationary phase disposed in at least two columns.

Embodiment 22. The method of any one of Embodiments 1-19, wherein the at least one stationary phase is more than one stationary phase disposed in at least two columns.

Embodiment 23. The method of Embodiment 21 or Embodiment 22, wherein at least two columns of said at least two columns are arranged in a SMB configuration to form a SMB zone, and wherein passing a feedstock stream comprising the composition through one stationary phase comprises passing the feedstock stream through the SMB zone.

Embodiment 24. The method of any one of Embodiments 1-23, wherein the feedstock stream further comprises a solvent selected from water, ethanol, acetone, ethyl acetate, acetonitrile, methanol, propanol, and a combination thereof.

Embodiment 25. The method of any one of Embodiments 1-24, wherein the feedstock stream further comprises ethanol.

Embodiment 26. The method of any one of Embodiments 1-25, further comprising:
obtaining the lysophosphatidylcholine from an enzymatic conversion of a phosphatidylcholine.

Embodiment 27. The method of Embodiment 26, wherein the enzymatic conversion is achieved by a lipase enzyme and/or a phospholipase enzyme.

Embodiment 28. The method of Embodiment 27, wherein the lipase enzyme and/or a phospholipase enzyme is immobilized.

Embodiment 29. The method of any one of Embodiments 26-28, further comprising: obtaining the phosphatidylcholine synthetically.

Embodiment 30. The method of any one of Embodiments 26-28, further comprising: obtaining the phosphatidylcholine from a natural source.

Embodiment 31. The method of Embodiment 30, wherein the natural source is fish oil, krill oil, egg, soybean, sunflower, marine microalgae, or a combination thereof.

Embodiment 32. The method of Embodiment 30 or Embodiment 31, wherein the natural source is krill oil.

Embodiment 33. The method of any one of Embodiments 1-32, further comprising:

drying the eluate stream to produce a purified composition comprising lysophosphatidylcholine.

Embodiment 34. A purified composition formed from the method of Embodiment 33.

Embodiment 35. The purified composition of Embodiment 34, wherein the composition comprises at least 60 wt. % of the lysophosphatidylcholine.

Embodiment 36. The purified composition of Embodiment 34 or Embodiment 35, wherein the composition comprises at least 70 wt. % of the lysophosphatidylcholine.

Embodiment 37. The purified composition of any one of Embodiments 34-36, wherein the composition comprises at least 80 wt. % of the lysophosphatidylcholine.

Embodiment 38. The purified composition of any one of Embodiments 34-37, wherein the composition comprises at least 90 wt. % of the lysophosphatidylcholine.

Embodiment 39. A dietary supplement comprising the purified composition of any one of Embodiments 34-38.

Embodiment 40. The dietary supplement of Embodiment 39, wherein the dietary supplement is a soft gel chewable.

Embodiment 41. A pharmaceutical composition comprising the purified composition of any one of Embodiments 34-38.

Embodiment 42. A method of treating and/or preventing a neurological disease or disorder comprising:

administering an effective amount of the purified composition of any one of Embodiments 34-38, the dietary supplement of Embodiment 39 or Embodiment 40, or the pharmaceutical composition of Embodiment 41 to a subject in need thereof.

Embodiment 43. The method of Embodiment 42, wherein the effective amount is an amount effective to increase docosahexaenoic acid (DHA), eicosapentaenoic acid (EPA), or a combination thereof in the brain of the subject.

Embodiment 44. The method of Embodiment 42 or Embodiment 43, wherein the neurological disease or disorder is depression, dementia, or a traumatic brain injury.

Embodiment 45. The method of Embodiment 42 or Embodiment 43, wherein the neurological disease or disorder is Alzheimer's disease or Parkinson's disease.

Embodiment 46. A purified composition comprising at least 60 wt. % of lysophosphatidylcholine.

Embodiment 47. The purified composition of Embodiment 46, wherein the composition comprises at least 80 wt. % of lysophosphatidylcholine.

Embodiment 48. The purified composition of Embodiment 76 or Embodiment 47, wherein the composition comprises at least 90 wt. % of lysophosphatidylcholine.

Embodiment 49. The purified composition of any one of Embodiments 46-48, wherein the composition comprises at least 95 wt. % of lysophosphatidylcholine.

Embodiment 50. The purified composition of any one of Embodiments 46-49, wherein the lysophosphatidylcholine is lysophosphatidylcholine-docosahexaenoic acid (LPC-DHA), lysophophatidylcholine-eicosapentaenoic acid (LPC-EPA), or a combination thereof.

Embodiment 51. The purified composition of any one of Embodiments 46-50, wherein the lysophosphatidylcholine is a combination of lysophosphatidylcholine-docosahexaenoic acid (LPC-DHA) and lysophophatidylcholine-eicosapentaenoic acid (LPC-EPA).

Embodiment 52. The purified composition of any one of Embodiments 46-50, wherein the lysophosphatidylcholine is lysophosphatidylcholine-docosahexaenoic acid (LPC-DHA).

Embodiment 53. The purified composition of Embodiment 51 or Embodiment 52, wherein the LPC-DHA is sn1-LPC-DHA.

Embodiment 54. The purified composition of Embodiment 51 or Embodiment 52, wherein the LPC-DHA is sn2-LPC-DHA.

Embodiment 55. The purified composition of any one of Embodiments 46-50, wherein the lysophosphatidylcholine is lysophophatidylcholine-eicosapentaenoic acid (LPC-EPA).

Embodiment 56. The purified composition of Embodiment 51 or Embodiment 55, wherein the LPC-EPA is sn1-LPC-EPA.

Embodiment 57. The purified composition of Embodiment 51 or Embodiment 55, wherein the LPC-EPA is sn2-LPC-EPA.

Embodiment 58. A dietary supplement comprising the purified composition of any one of Embodiments 46-57.

Embodiment 59. The dietary supplement of Embodiment 58, wherein the dietary supplement is a soft gel chewable.

Embodiment 60. A pharmaceutical composition comprising the purified composition of any one of Embodiments 46-57.

Embodiment 61. A method of treating and/or preventing a neurological disease or disorder comprising: administering an effective amount of the purified composition of any one of Embodiments 46-57, the dietary supplement of Embodiment 58 or Embodiment 59, or the pharmaceutical composition of Embodiment 60 to a subject in need thereof.

Embodiment 62. The method of Embodiment 61, wherein the effective amount is an amount effective to increase docosahexaenoic acid (DHA), eicosapentaenoic acid (EPA), or a combination thereof in the brain of the subject.

Embodiment 63. The method of Embodiment 61 or Embodiment 62, wherein the neurological disease or disorder is depression, dementia, or a traumatic brain injury.

Embodiment 64. The method of Embodiment 61 or Embodiment 62, wherein the neurological disease or disorder is Alzheimer's disease or Parkinson's disease.

The foregoing exemplary embodiments of the disclosure numbered 1-64 are non-limiting. Other exemplary embodiments are apparent from the entirety of the description herein. As will be apparent to those of skill in the art upon reading this disclosure, each of the individually numbered embodiments may be used or combined with any of the preceding or following individually numbered aspects.

EXAMPLES

The following examples are provided to illustrate the present disclosure. These examples are shown for illustrative purposes, and any disclosures embodied therein should not be limited thereto.

Example 1—Preparation of LPC-DHA and LPC-EPA by Lipase Digestion of Krill Oil 10 g of krill oil (Superba2™) was dissolved in 100 ml of 95% (v/v) ethanol in water by stirring at room temperature for 10 minutes, and the resulting solution was centrifuged at 1000 g for 10 minutes to remove the suspended particles. The krill oil (Superba2™) used in this example had an initial composition profile as shown in FIG. 1 and set forth in Table 1.

TABLE 1

Krill Oil Composition Profile

| | Total Phospholipids (wt. %) | Phosphatidylcholine (wt. %) | Choline (wt. %) |
|---|---|---|---|
| Lipids | 43 | 38 | 5 |
| | Total n-3 PUFA (wt. %) | EPA (wt. %) | DHA (wt. % |
| Fatty Acid Profile | 24.2 | 14.2 | 6.9 |

Figure 2:
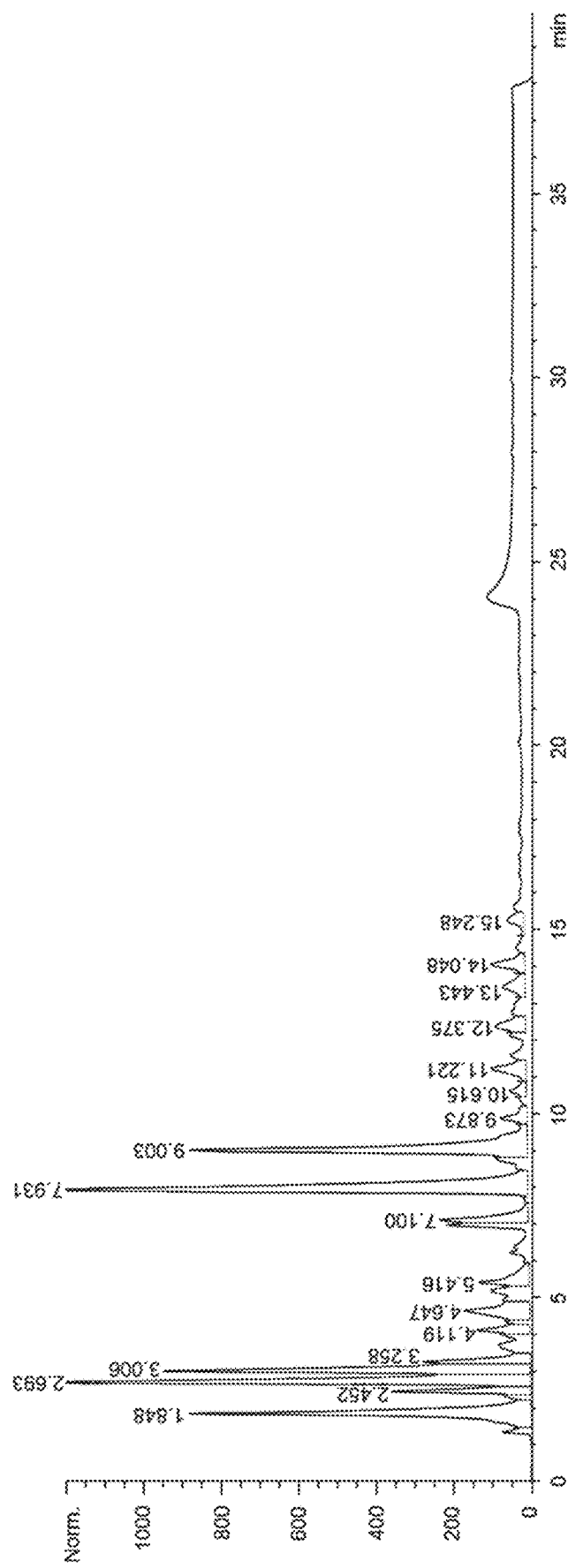
FIG. 2 is a high performance liquid chromatography (HPLC) chromatogram of krill oil after 24 hours of lipase digestion at 50° C.

An immobilized acrylic lipase enzyme (Novozyme® 435, commercially available from Sigma-Aldrich, expressed in *Aspergillus niger*, 10 g) was added to the supernatant solution, flushed with nitrogen, and incubated at 50° C. for 24 hours in a metabolic shaker in the dark. The suspension was centrifuged at 1000 g for 10 minutes and the supernatant was separated from the immobilized acrylic lipase enzyme. The acrylic lipase enzyme was washed twice with 50 ml of 95% (v/v) ethanol in water and the supernatant was collected as before. The digested solution was subjected to HPLC and LC/MS analysis and the results are set forth in FIG. 2.

Figure 3:
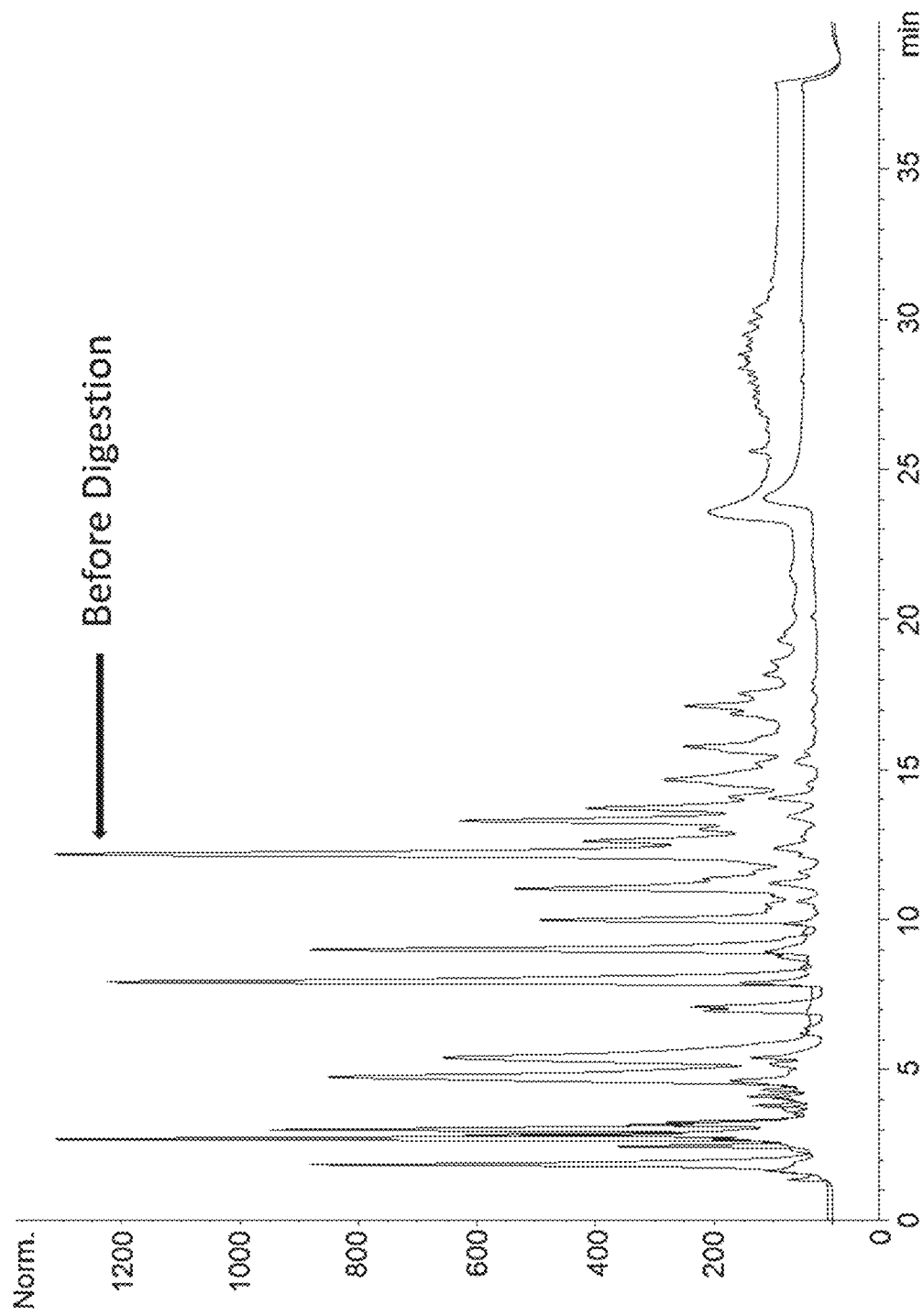
FIG. 3 is an overlay of a high performance liquid chromatography (HPLC) chromatogram of krill oil before lipase digestion and a high performance liquid chromatography (HPLC) chromatogram of krill oil after 24 hours of lipase digestion at 50° C.

Analysis was performed using an Agilent 1100 series on a 4.6×150 mm C18, 3 µM column (Orochem Technologies Inc.) with the following parameters:
Temperature: 50° C.
Flow Rate: 1 ml/min
Wavelength: 215 nm
Mobile Phase: gradient of ethanol and water
As is apparent from the results set forth in FIG. 1, FIG. 2, and the overlay of the before digestion and after digestion shown in FIG. 3, the immobilized acrylic enzyme converts most of the phosphatidylcholine to lysophosphatidylcholine.

Example 2—Purification of LPC-DHA and LPC-EPA by Column Chromatography

A polydivinylbenzene resin (Chromalite® PCG1200C, commercially available from Purolite® Life Sciences) was suspended in 85% (v/v) ethanol in water and packed into a 22×300 mm stainless steel column. The column was placed in a water bath maintained at 50° C. The column was equilibrated with 4 column volumes of 85% (v/v) ethanol in water at 3 mL/min. The digested krill oil obtained from Example 1 (2 g) was diluted in 85% (v/v) ethanol in water and loaded on to the column. Elution was carried out with 85% (v/v) ethanol in water at 3 mL/min and collected as 30 mL fractions in Pools as specified in FIG. 4A. Pool 1 was subjected to HPLC and mass spectrometry analysis.

The analysis was carried out using an AB ExionLC™ ultra high performance liquid chromatograph UHPLC (commercially available from Sciex™) hooked up to an AB Triple Quad 4500 Mass Spectrometer (commercially available from Sciex™). The UHPLC utilized a Gazelle C18, 2.1×50 mm UHPLC column (Orochem Technologies Inc.) with the following parameters:
Temperature: 40° C.
Flow Rate: 0.2 mL/min
Injection Size: A 10 µL
Mobile phase: gradient of 15 mM ammonium acetate in ethanol/0.1% formic acid and 15 mM ammonium acetate in water/0.1% formic acid.

The mass spectrometer was run in negative mode using Product Ion Scan mode. In this mode the parent ion is isolated and fragmented by colliding the ion with an inert gas in the second quadrupole. All resulting fragments of the collision are monitored and detected as the fragment ions of the parent ion, which results in the parent ions being detected as formate adducts.

Figure 5A:
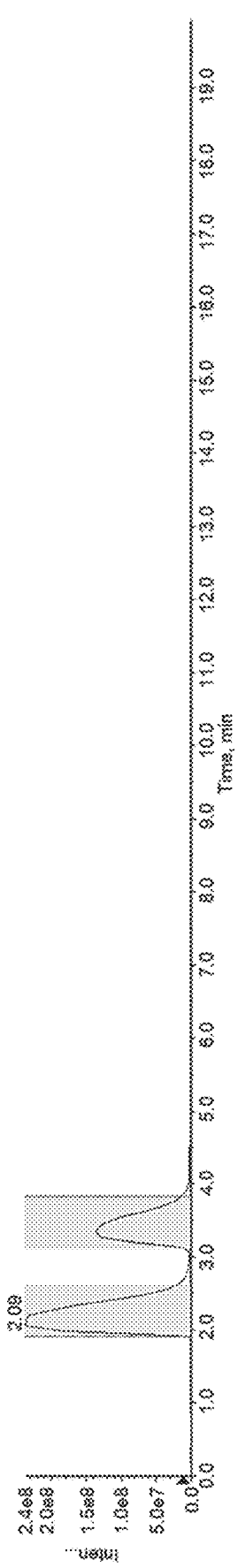
FIG. 5A is a mass spectrometry (MS) chromatogram of a purified mixture of LPC-EPA (2 minutes) and LPC-DHA (3 minutes).
Figure 5B:
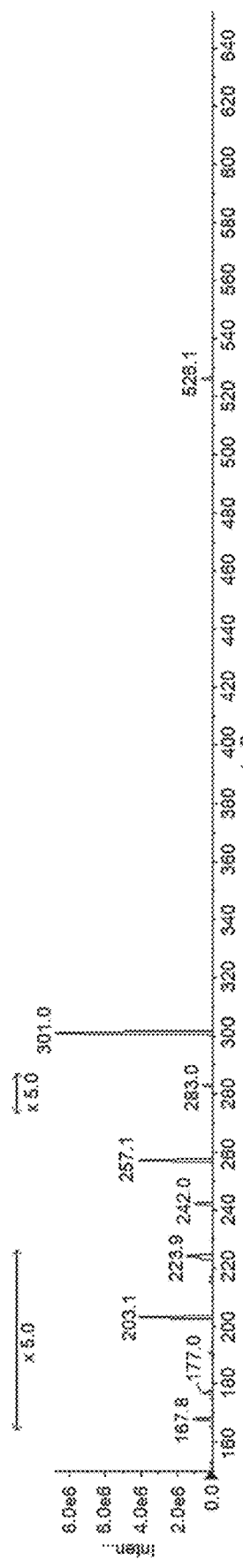
FIG. 5B is a mass spectrometry (MS) ion spectrum of the LPC-EPA peak at 2 minutes of the mass spectrometry (MS) chromatogram shown in FIG. 5A.
Figure 5C:
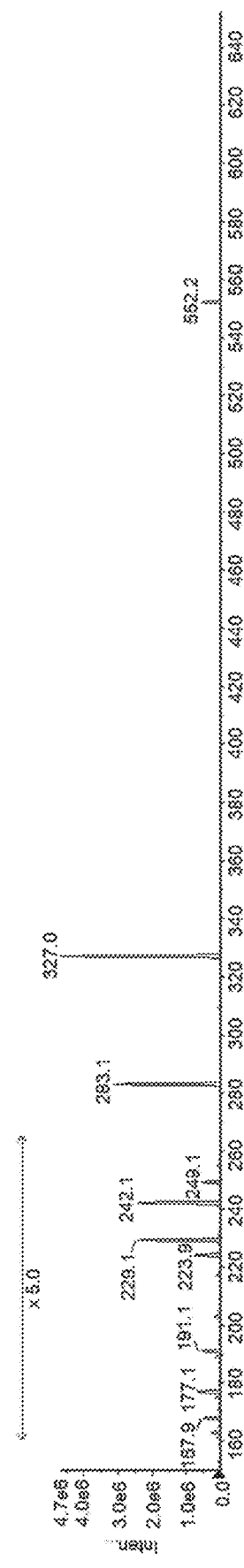
FIG. 5C is a mass spectrometry (MS) ion spectrum of the LPC-DHA peak at 3 minutes of the mass spectrometry (MS) chromatogram shown in FIG. 5A.

LPC-EPA and LPC-DHA were identified by retention time and mass fingerprinting after fragmentation of the parent ion, as set forth in FIGS. 5A-5C, and the peaks are identified in FIG. 4B. As is apparent from FIGS. 4A-5C, the divinylbenzene resin successfully separates LPC-EPA and LPC-DHA from the digested mixture, thereby providing a purified composition containing LPC-EPA and LPC-DHA.

Figure 6:
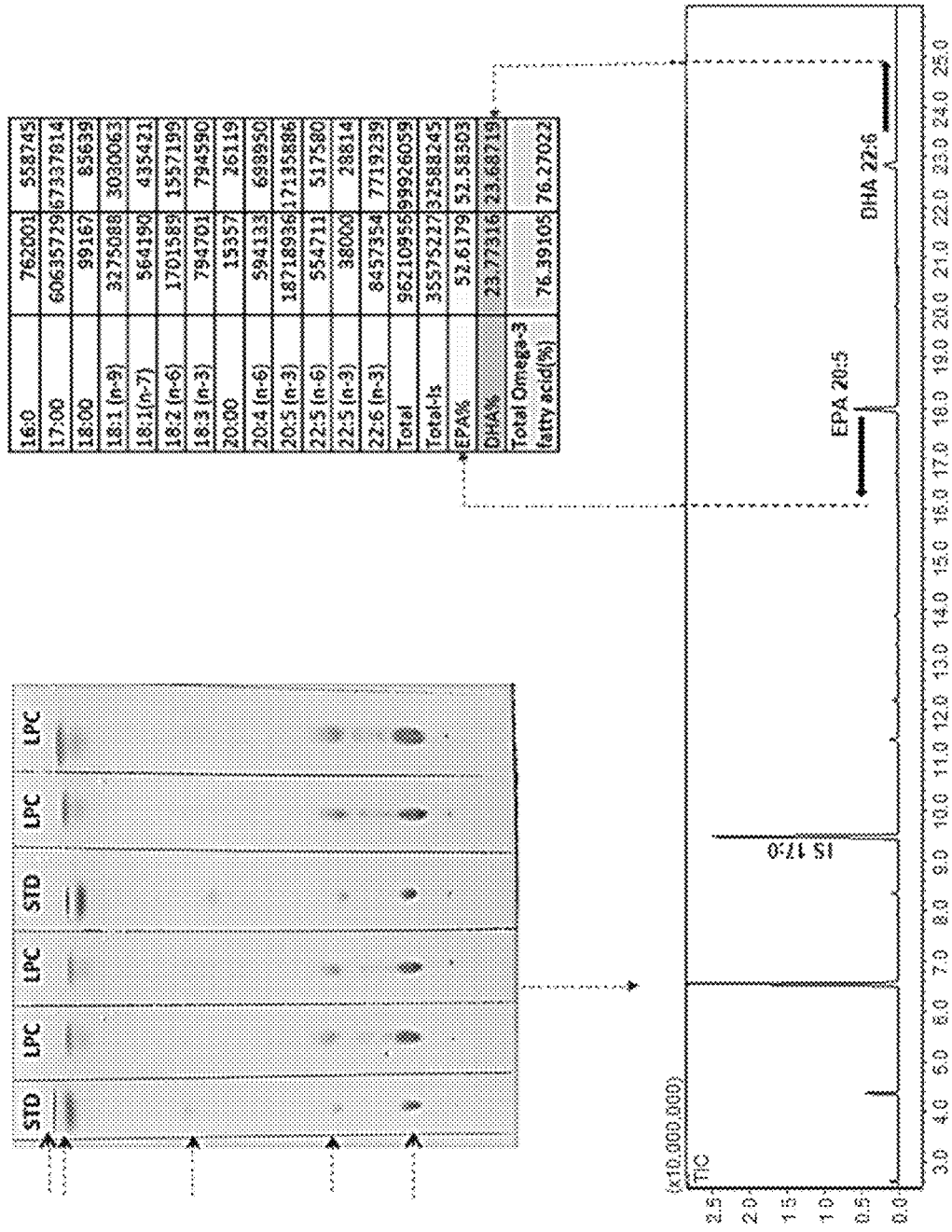
FIG. 6 shows a thin layer chromatography (TLC) chromatogram and a gas chromatography mass spectrometry (GCMS) analysis of Pool 1 set forth in FIG. 4A.

Purified Pool 1 was further analyzed by thin layer chromatography (TLC) and gas chromatography (GC) as set forth in FIG. 6. As is apparent from the results of the GC analysis, the purified composition contains approximately 53 wt. % LPC-EPA and 24 wt. % LPC-DHA.

Example 3—Preparation of sn-2-DHA-LPC from Synthetic 16:0-22:6 Phosphatidylcholine 10 mg of synthetic 16:0-22:6 phosphatidylcholine (i.e., phosphatidylcholine palmitic acid/docosahexaenoic acid) was dissolved in 0.5 mL of 95% (v/v) ethanol in water.

An immobilized acrylic lipase enzyme (Novozyme® 435, commercially available from Sigma-Aldrich, expressed in *Aspergillus niger*, 20 mg) was added to the solution, flushed with nitrogen, and incubated at 50° C. for 24 hours in a metabolic shaker in the dark. The suspension was centrifuged at 1000 g for 10 minutes and the supernatant was separated from the immobilized acrylic lipase enzyme. The starting synthetic 16:0-22:6 phosphatidylcholine and the digested solution were subjected to HPLC analysis and the results are set forth in FIG. 7A and FIG. 7B, respectively.

Analysis was performed using an Agilent 1100 series on a 4.6×150 mm C18, 3 µM column (Orochem Technologies Inc.) with the following parameters:
Temperature: 50° C.
Flow Rate: 1 ml/min
Wavelength: 215 nm
Mobile Phase: gradient of ethanol and water
In addition, the chromatogram of the digested solution of synthetic 16:0-22:6 phosphatidylcholine was compared with the chromatogram of the purified LPC-EPA/LPC-DHA pool obtained from the digestion of krill oil as set forth in Example 1. The overlay of the chromatograms is shown in FIG. 8.

Figure 7A:
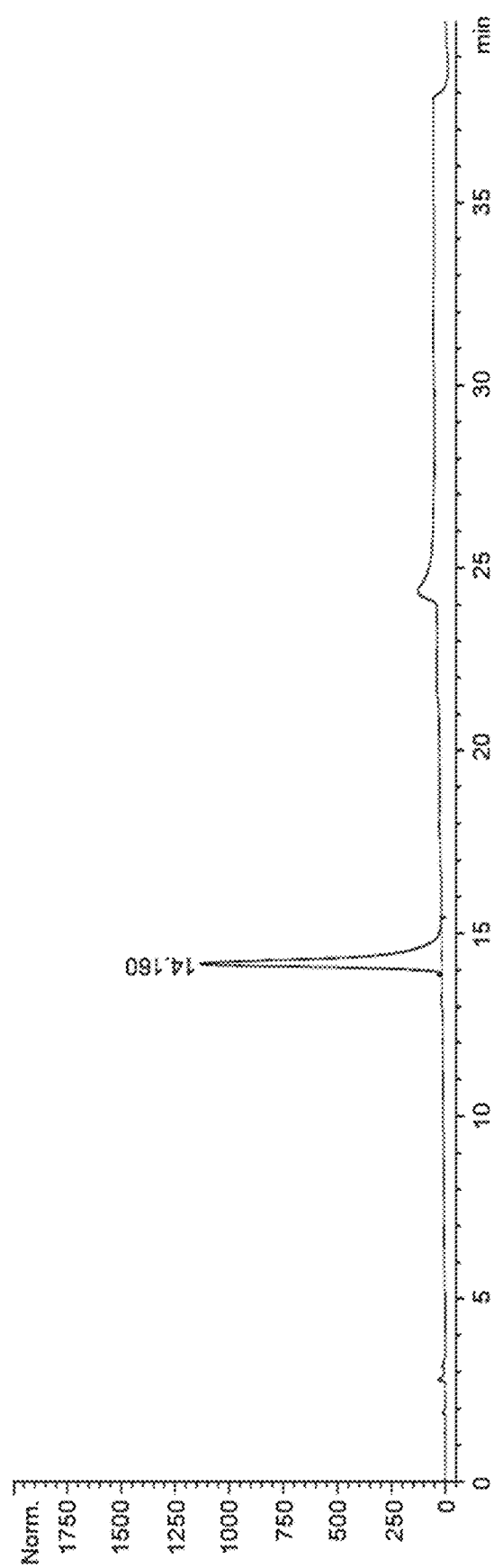
FIG. 7A is a high performance liquid chromatography (HPLC) chromatogram of synthetic 16:0-22:6 phosphatidylcholine, i.e., phosphatidylcholine palmitic acid/docosahexaenoic acid.
Figure 7B:
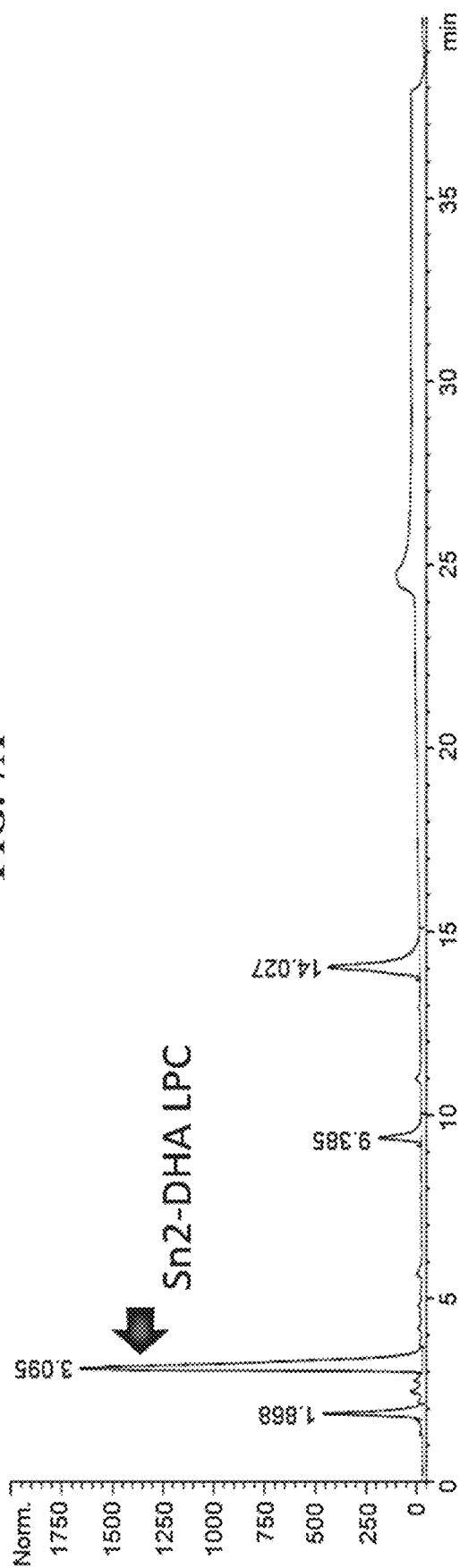
FIG. 7B is a high performance liquid chromatography (HPLC) chromatogram of synthetic 16:0-22:6 phosphatidylcholine after 24 hours of lipase digestion at 50° C.
Figure 8:
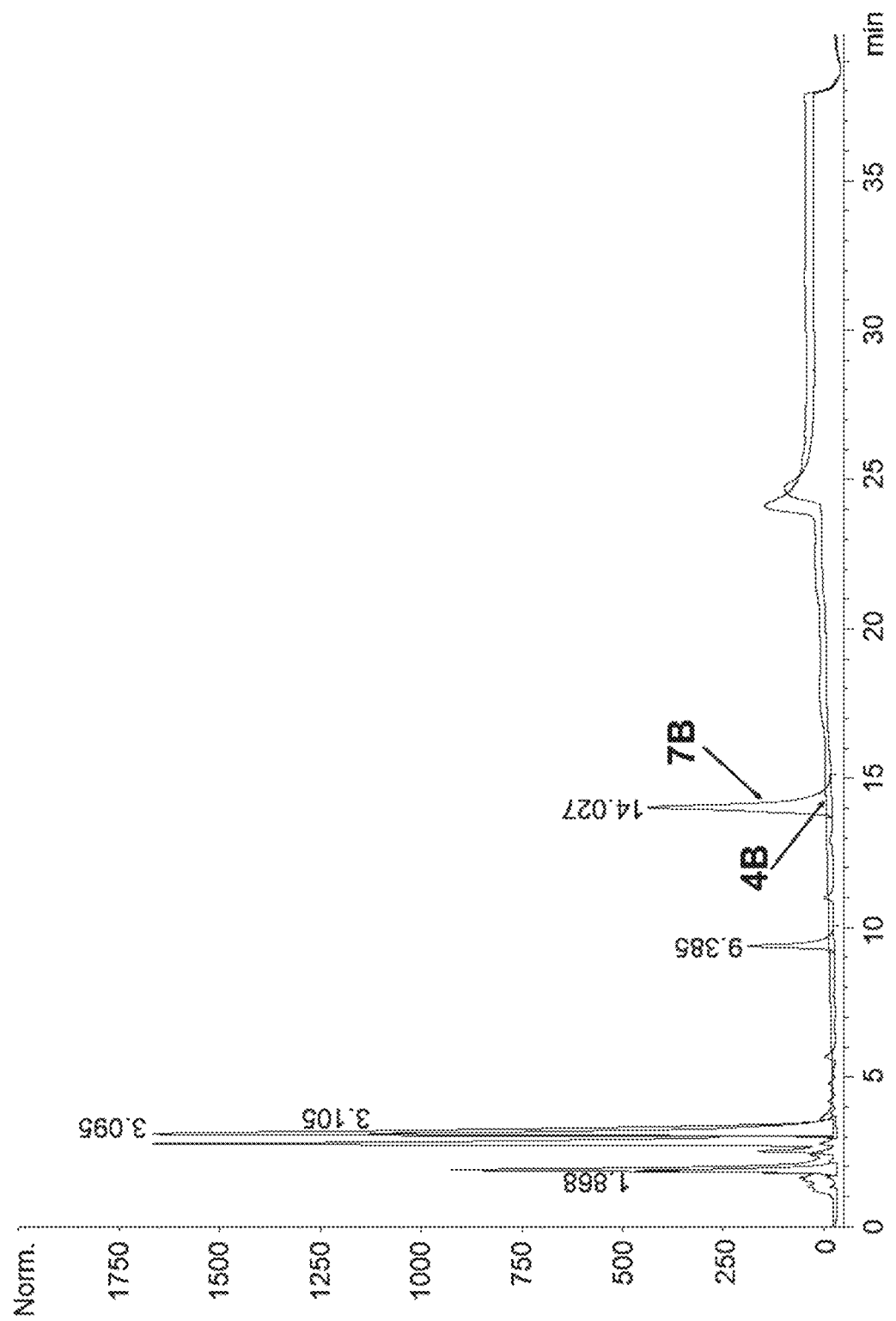
FIG. 8 is an overlay of a high performance liquid chromatography (HPLC) chromatogram of purified LPC-EPA and LPC-DHA obtained from Pool 1 set forth in FIG. 4A (labelled 4B in FIG. 8) and a high performance liquid chromatography (HPLC) chromatogram of synthetic 16:0-22:6 phosphatidylcholine after 24 hours of lipase digestion at 50° C. (labelled 7B in FIG. 8).

As is apparent from the results set forth in FIG. 7A, FIG. 7B, and the overlay of FIGS. 4B and 7B shown in FIG. 8, the immobilized acrylic enzyme effectively converts synthetic 16:0-22:6 phosphatidylcholine to LPC-DHA, and more particularly to sn2-LPC-DHA.

Example 4—Preparation of Pure LPC-DHA and LPC-EPA by Column Chromatography

A polystyrene/divinylbenzene resin (Sepabeads™, commercially available from Mitsubishi Chemical Corporation) was suspended in ethanol and packed into a 10×250 mm stainless steel column. The column was equilibrated with 4 column volumes of 80% (v/v) ethanol in water at 0.5 mL/min. Purified Pool 1, obtained from Example 2 (150 mg)

was diluted in 80% (v/v) ethanol in water (2 mL) and loaded on to the column. Elution was carried out with 80% (v/v) ethanol in water at 0.5 mL/min and collected as 2 mL fractions and subjected to HPLC and mass spectrometry analysis.

The analysis was carried out using an AB ExionLC™ ultra high performance liquid chromatograph UHPLC (commercially available from Sciex™) hooked up to an AB Triple Quad 4500 Mass Spectrometer (commercially available from Sciex™). The UHPLC utilized a Gazelle C18, 2.1×50 mm UHPLC column (Orochem Technologies Inc.) with the following parameters:

Temperature: 40° C.
Flow Rate: 0.2 mL/min
Injection Size: A 10 µL
Mobile phase: gradient of 15 mM ammonium acetate in ethanol/0.1% formic acid and 15 mM ammonium acetate in water/0.1% formic acid.

The mass spectrometer was run in negative mode using Product Ion Scan mode. In this mode the parent ion is isolated and fragmented by colliding the ion with an inert gas in the second quadrupole. All resulting fragments of the collision are monitored and detected as the fragment ions of the parent ion, which results in the parent ions being detected as formate adducts.

Figure 9:
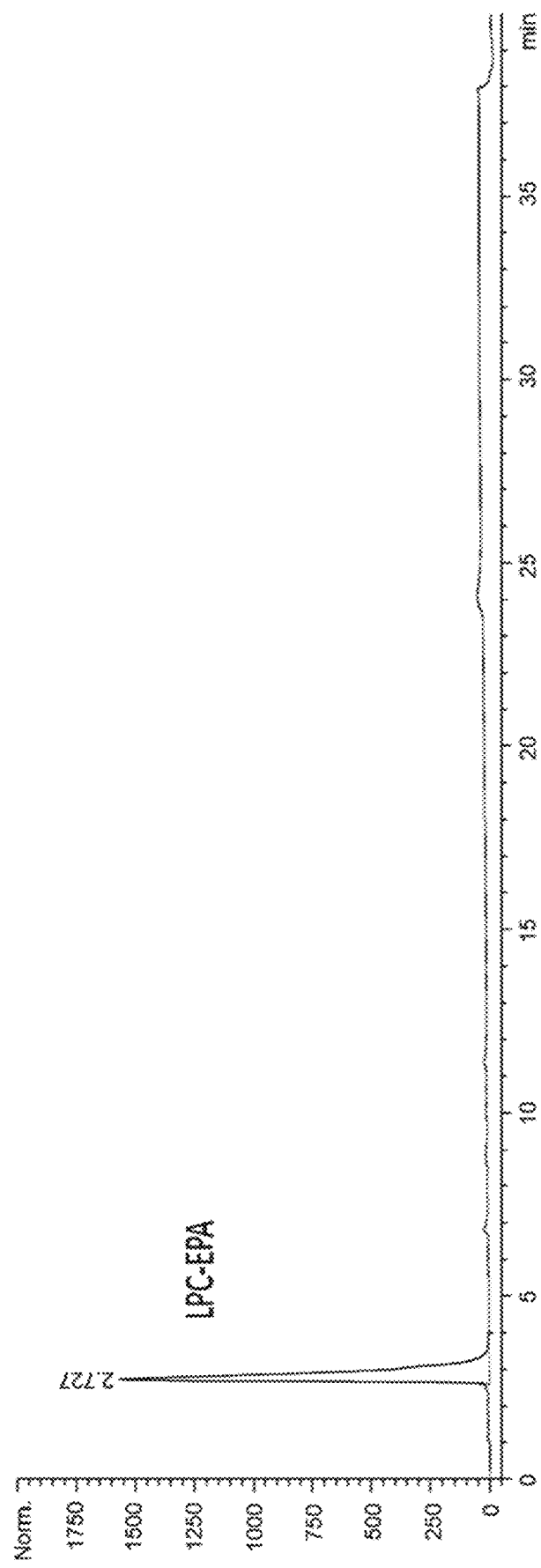
FIG. 9 is a high performance liquid chromatography (HPLC) chromatogram of purified lysophophatidylcholine-eicosapentaenoic acid (LPC-EPA).
Figure 10:
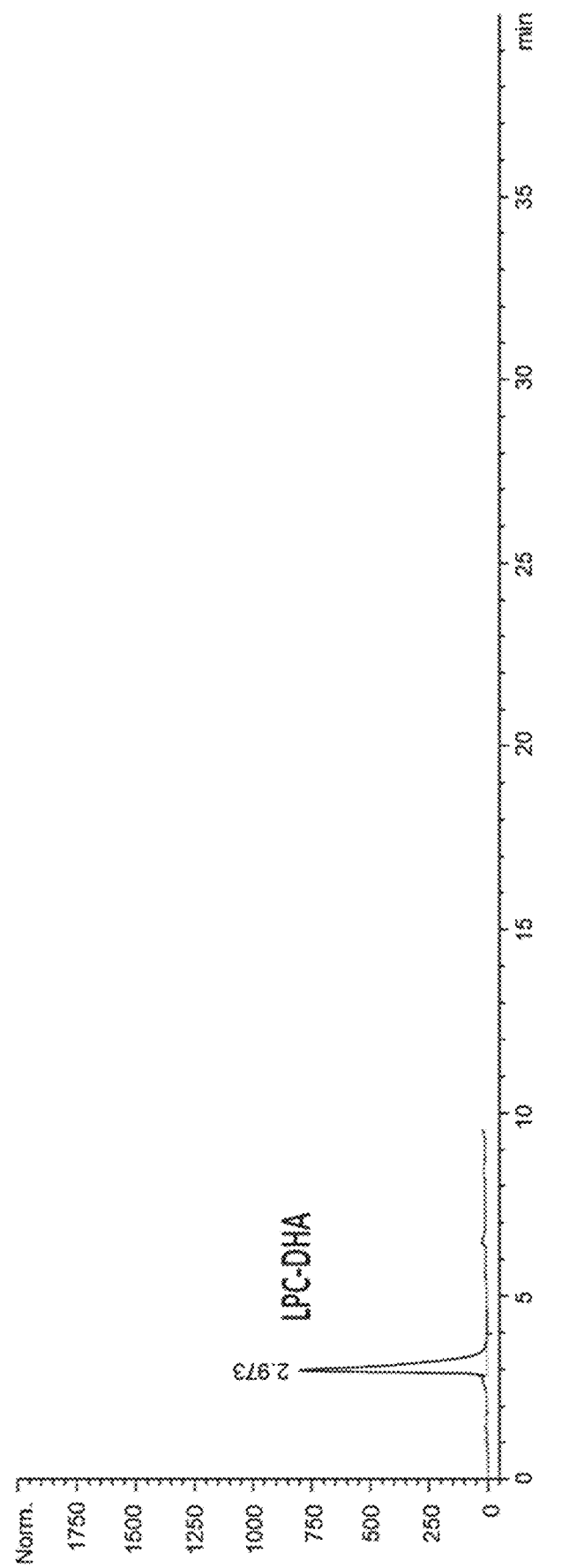
FIG. 10 is a high performance liquid chromatography (HPLC) chromatogram of purified lysophosphatidylcholine-docosahexaenoic acid (LPC-DHA).

LPC-EPA and LPC-DHA were isolated separately as pure fractions as depicted in FIGS. 9 and 10. As is apparent from the retention times of 2.727 minutes and 2.973 minutes, purified LPC-EPA is depicted in FIG. 9, and purified LPC-DHA is depicted in FIG. 10. Thus, the polystyrene/divinylbenzene resin successfully separates LPC-EPA and LPC-DHA from the pooled fractions obtained in Example 2, thereby providing purified compositions containing LPC-EPA and LPC-DHA.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims, while the description, abstract and drawings are not to be used to limit the scope of the invention. The invention is specifically intended to be as broad as the claims below and their equivalents.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. As used herein, the term "exemplary" indicates an example thereof and does not suggest a best or optimal of the recited item. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of purifying a lysophosphatidylcholine from a composition containing the lysophosphatidylcholine and at least one impurity, the method comprising:
   passing a feedstock stream comprising the composition through at least one reverse phase or hydrophobic stationary phase to provide an eluate stream having a higher purity of the lysophosphatidylcholine than in the feedstock stream.

2. The method of claim 1, wherein the lysophosphatidylcholine is lysophosphatidylcholine-docosahexaenoic acid (LPC-DHA), lysophosphatidylcholine-eicosapentaenoic acid (LPC-EPA), or a combination thereof.

3. The method of claim 1, wherein the lysophosphatidylcholine is lysophosphatidylcholine-docosahexaenoic acid (LPC-DHA).

4. The method of claim 1, wherein the lysophosphatidylcholine is lysophosphatidylcholine-eicosapentaenoic acid (LPC-EPA).

5. The method of claim 1, wherein the stationary phase comprises a divinylbenzene-based adsorbent having at least one of:
   (i) an average particle diameter of 20 microns to 600 microns,
   (ii) an average surface area of 300 $m^2/g$ to 900 $m^2/g$,
   (iii) an average porosity of 75 Å to 1000 Å,
   (iv) an average water content of 35% to 80%, and
   (v) an average bulk density of 0.45 g/mL to 0.9 g/mL.

6. The method of claim 5, wherein the divinylbenzene-based adsorbent comprises a polystyrene-divinylbenzene adsorbent, a polydivinylbenzene adsorbent, or a combination thereof.

7. The method of claim 1, wherein said at least one impurity comprises at least one of phospholipids, free fatty acids, triacylglycerols (TAGs), diacylglycerols (DAGs), monoacylglycerols (MAGs), glycerol, sterols, tocopherols, vitamin A, flavonoids, minerals, and mixtures thereof.

8. The method of claim 1, wherein the at least one stationary phase is disposed in a single column or more than one column in series.

9. The method of claim 1, wherein the at least one stationary phase is one stationary phase disposed in at least two columns.

10. The method of claim 9, wherein at least two columns of said at least two columns are arranged in a SMB configuration to form a SMB zone, and wherein passing a feedstock stream comprising the composition through one stationary phase comprises passing the feedstock stream through the SMB zone.

11. The method of claim 1, wherein the at least one stationary phase is more than one stationary phase disposed in at least two columns.

12. The method of claim 11, wherein at least two columns of said at least two columns are arranged in a SMB configuration to form a SMB zone, and wherein passing a feedstock stream comprising the composition through one stationary phase comprises passing the feedstock stream through the SMB zone.

13. The method of claim 1, wherein the feedstock stream further comprises a solvent selected from water, ethanol, acetone, ethyl acetate, acetonitrile, methanol, propanol, and a combination thereof.

14. The method of claim 1, further comprising:
   obtaining the lysophosphatidylcholine from an enzymatic conversion of a phosphatidylcholine.

15. The method of claim 1, further comprising:
   drying the eluate stream to produce a purified composition comprising lysophosphatidylcholine.

* * * * *